(12) United States Patent
Stibich et al.

(10) Patent No.: US 10,245,341 B2
(45) Date of Patent: Apr. 2, 2019

(54) ROOM AND AREA DISINFECTION UTILIZING PULSED LIGHT WITH MODULATED POWER FLUX AND LIGHT SYSTEMS WITH VISIBLE LIGHT COMPENSATION BETWEEN PULSES

(71) Applicant: Xenex Disinfection Services, LLC., San Antonio, TX (US)

(72) Inventors: Mark A. Stibich, Santa Fe, NM (US); Charles Dale, San Antonio, TX (US); Edward C. Guerrero, Jr., San Antonio, TX (US); Paul P. Froutan, Katy, TX (US); Sarah E. Simmons, San Antonio, TX (US); Boris Ciorneiu, Great Falls, VA (US)

(73) Assignee: Xenex Disinfection Services, LLC., San Antonio, TX (US)

(*) Notice: Subject to any disclaimer, the term of this patent is extended or adjusted under 35 U.S.C. 154(b) by 0 days.

(21) Appl. No.: 15/989,394

(22) Filed: May 25, 2018

(65) Prior Publication Data

US 2018/0272017 A1 Sep. 27, 2018

Related U.S. Application Data

(60) Division of application No. 15/454,158, filed on Mar. 9, 2017, which is a continuation of application No. PCT/US2015/051010, filed on Sep. 18, 2015.
(Continued)

(51) Int. Cl.
*A61L 2/10* (2006.01)
*A61L 2/24* (2006.01)
*A23L 3/28* (2006.01)

(52) U.S. Cl.
CPC .............. *A61L 2/10* (2013.01); *A23L 3/28* (2013.01); *A61L 2/24* (2013.01); *A23V 2002/00* (2013.01); *A61L 2202/14* (2013.01)

(58) Field of Classification Search
CPC ..................................... A61L 2/10; A61L 2/24
(Continued)

(56) References Cited

U.S. PATENT DOCUMENTS 4,229,658 A   10/1980  Gonser
4,575,636 A    3/1986  Caprari
(Continued)

FOREIGN PATENT DOCUMENTS

CA        2569130       6/2008
CN      101890174      11/2010
(Continued)

OTHER PUBLICATIONS

Intellectual Property Office, Examination Report for Great Britain Patent Application No. GB1705340.6 dated May 31, 2017, 2 pgs.
(Continued)

*Primary Examiner* — Kevin Joyner
(74) *Attorney, Agent, or Firm* — Egan Peterman Enders Huston

(57) ABSTRACT

Disinfection methods and apparatuses are provided which generate pulses of germicidal light at a frequency greater than 20 Hz and project the pulses of light to surfaces at least 1.0 meter from the disinfection apparatus. The pulses of light comprise a pulse duration and an energy flux sufficient to generate a power flux between approximately 200 W/m² and approximately 5000 W/m² of ultraviolet light in the wavelength range between 200 nm and 320 nm at the surfaces. Other disinfection methods and apparatuses are provided which generate pulses of light comprising germicidal light and visible light from a germicidal light source and generate
(Continued)

pulses of light from a visible light source that is distinct from the germicidal light source. The projections of visible light from the light sources produce a continuous stream of visible light or a collective stream of visible light pulsed at a frequency greater than 60 Hz.

13 Claims, 4 Drawing Sheets

Related U.S. Application Data

(60) Provisional application No. 62/052,036, filed on Sep. 18, 2014.

(58) Field of Classification Search
USPC .......................................................... 422/24
See application file for complete search history.

(56) References Cited

U.S. PATENT DOCUMENTS

| | | |
|---|---|---|
| 4,910,942 A | 3/1990 | Dunn et al. |
| 5,144,146 A | 9/1992 | Wekhof |
| 5,344,433 A | 9/1994 | Talmore |
| 5,364,645 A | 11/1994 | Lagunas-Solar et al. |
| 5,433,344 A | 7/1995 | Fulton et al. |
| 5,659,287 A | 8/1997 | Donati et al. |
| 5,673,999 A | 10/1997 | Koenck |
| 5,689,364 A | 11/1997 | McGregor et al. |
| 5,744,094 A | 4/1998 | Castberg |
| 5,768,853 A | 6/1998 | Bushnell |
| 5,925,885 A | 8/1999 | Clark |
| 6,264,802 B1 | 7/2001 | Kamrukov et al. |
| 6,264,836 B1 | 7/2001 | Lantis |
| 6,403,030 B1 | 6/2002 | Horton |
| 6,447,720 B1 | 9/2002 | Horton |
| 6,465,799 B1 | 10/2002 | Kimble |
| 6,468,433 B1 | 10/2002 | Tribelski |
| 6,566,659 B1 | 5/2003 | Clark |
| 6,656,424 B1 | 12/2003 | Deal |
| 6,774,382 B2 | 8/2004 | Yoshida |
| 7,175,814 B2 | 2/2007 | Dionisio |
| 7,930,066 B2 | 4/2011 | Eluik |
| 8,021,608 B2 | 9/2011 | Brown-Skrobot et al. |
| 8,142,713 B2 | 3/2012 | Gordon |
| 8,203,126 B2 | 6/2012 | Rocha-Alvarez |
| 8,318,089 B2 | 11/2012 | Brown-Skrobot et al. |
| 8,354,060 B2 | 1/2013 | Horne et al. |
| 8,470,239 B1 | 6/2013 | Kerr |
| 8,497,491 B2 | 7/2013 | Goldshtein et al. |
| 8,816,301 B2 | 8/2014 | Stibich et al. |
| 8,907,304 B2 | 12/2014 | Kreitenberg |
| 9,114,182 B2 | 8/2015 | Stibich et al. |
| 9,165,756 B2 | 10/2015 | Stibich et al. |
| 9,504,345 B2 | 11/2016 | Stibich et al. |
| 9,517,284 B1 | 12/2016 | Stibich et al. |
| 9,744,255 B2 | 8/2017 | Stibich |
| 9,867,894 B2 | 1/2018 | Stibich et al. |
| 2002/0161418 A1 | 10/2002 | Wilkens et al. |
| 2003/0044311 A1 | 3/2003 | Sousa et al. |
| 2004/0052702 A1 | 3/2004 | Shuman et al. |
| 2004/0120844 A1 | 6/2004 | Tribelsky et al. |
| 2004/0175290 A1 | 9/2004 | Scheir et al. |
| 2005/0055070 A1 | 3/2005 | Jones et al. |
| 2005/0143793 A1 | 6/2005 | Korman et al. |
| 2005/0151937 A1 | 7/2005 | Sugitani |
| 2005/0152146 A1 | 7/2005 | Owen et al. |
| 2005/0186108 A1 | 8/2005 | Fields |
| 2005/0202395 A1 | 9/2005 | Edrich et al. |
| 2006/0009822 A1 | 1/2006 | Savage et al. |
| 2006/0216193 A1 | 9/2006 | Johnson et al. |
| 2006/0228251 A1 | 10/2006 | Schneberger et al. |
| 2007/0038206 A1 | 2/2007 | Altshuler et al. |
| 2007/0192986 A1 | 8/2007 | Garcia |
| 2007/0248487 A1 | 10/2007 | Kay et al. |
| 2007/0255266 A1 | 11/2007 | Cumbie et al. |
| 2007/0257205 A1 | 11/2007 | Rocha-Alvarez et al. |
| 2008/0112845 A1 | 5/2008 | Dunn |
| 2008/0150443 A1 | 6/2008 | Tipton |
| 2008/0199353 A1 | 8/2008 | Mlodzinski et al. |
| 2008/0199354 A1 | 8/2008 | Gordon |
| 2008/0213128 A1 | 9/2008 | Rudy et al. |
| 2008/0305004 A1 | 12/2008 | Anderson et al. |
| 2008/0310996 A1 | 12/2008 | Kim et al. |
| 2009/0004047 A1 | 1/2009 | Hunter et al. |
| 2009/0123343 A1 | 5/2009 | Kwiatkowski |
| 2009/0129974 A1 | 5/2009 | McEllen |
| 2009/0191100 A1 | 7/2009 | Deal |
| 2009/0304553 A1 | 12/2009 | Gordon |
| 2009/0314308 A1 | 12/2009 | Kim et al. |
| 2009/0323181 A1 | 12/2009 | Andrews et al. |
| 2010/0069898 A1 | 3/2010 | O'Neil et al. |
| 2010/0078574 A1 | 4/2010 | James et al. |
| 2010/0104471 A1 | 4/2010 | Harmon et al. |
| 2010/0000948 A1 | 7/2010 | Park |
| 2010/0183476 A1 | 7/2010 | Lu |
| 2010/0246169 A1 | 9/2010 | Anderson et al. |
| 2011/0073774 A1 | 3/2011 | Taylor et al. |
| 2011/0206554 A1 | 8/2011 | Anderle et al. |
| 2011/0305597 A1 | 12/2011 | Farren |
| 2012/0045730 A1 | 2/2012 | Sayder et al. |
| 2012/0093688 A1 | 4/2012 | Harmon et al. |
| 2012/0119108 A1 | 5/2012 | Goldshtein et al. |
| 2012/0126134 A1 | 5/2012 | Deal et al. |
| 2012/0156094 A1 | 6/2012 | Gordon |
| 2012/0223216 A1 | 9/2012 | Flaherty et al. |
| 2012/0305787 A1 | 12/2012 | Henson |
| 2013/0048876 A1 | 2/2013 | Crawford |
| 2013/0078142 A1 | 3/2013 | Gordon |
| 2014/0060095 A1 | 3/2014 | Shur et al. |
| 2014/0061509 A1 | 3/2014 | Shur et al. |
| 2014/0241941 A1 | 8/2014 | Kreitenberg |
| 2014/0291552 A1 | 10/2014 | Schumacher |
| 2014/0303547 A1 | 10/2014 | Loupis et al. |
| 2015/0367008 A1* | 12/2015 | Romo ................... A61L 2/10 422/24 |
| 2016/0137276 A1 | 5/2016 | Salters et al. |
| 2016/0296649 A1 | 10/2016 | Ramanand |
| 2017/0173195 A1 | 3/2017 | Stibich et al. |
| 2017/0216472 A1 | 8/2017 | Stibich et al. |

FOREIGN PATENT DOCUMENTS

| | | |
|---|---|---|
| DE | 149020 | 6/1981 |
| EP | 0464688 | 1/1992 |
| EP | 2172097 | 4/2010 |
| EP | 2174670 | 4/2010 |
| EP | 2465543 | 6/2012 |
| GB | 2203283 | 10/1988 |
| GB | 2399216 | 4/2003 |
| JP | 20058218850 | 8/2005 |
| JP | 2005261954 | 9/2005 |
| JP | 2005261984 | 9/2005 |
| JP | 2005305031 | 11/2005 |
| JP | 2007037761 | 2/2007 |
| JP | 2014030763 | 2/2014 |
| KR | 1020000062691 | 10/2000 |
| RU | 2001629 | 10/1993 |
| RU | 2001882 | 10/1993 |
| WO | 9715332 | 5/1997 |
| WO | 0078678 | 12/2000 |
| WO | 01/061419 | 8/2001 |
| WO | 2003/021632 | 8/2002 |
| WO | 2003061382 | 7/2003 |
| WO | 2004/108959 | 6/2004 |
| WO | 06/070281 | 7/2006 |
| WO | 2007/123859 | 4/2007 |
| WO | 2007067654 | 6/2007 |
| WO | 07081401 | 7/2007 |
| WO | 07/089312 | 8/2007 |
| WO | 2010/115183 | 10/2010 |
| WO | 2010134838 | 11/2010 |
| WO | 12/142427 | 10/2012 |
| WO | 2014051906 | 8/2013 |

(56) References Cited

FOREIGN PATENT DOCUMENTS

| WO | 2014022717 | 2/2014 |
|---|---|---|
| WO | 2014088580 | 6/2014 |
| WO | 2014100493 | 6/2014 |
| WO | 2015/116876 | 8/2015 |

OTHER PUBLICATIONS

Intellectual Property Office, Examination Report for Great Britain Patent Application No. GB1705340.6 dated Dec. 22, 2017, 3 pgs.
Sterilize, "Fast, Effective Ultraviolet Room Disinfection" brochure, date not available, 4 pgs.
Australian Government, IP Australia, Notice of Acceptance for Australian Patent Application No. 2015317384, Jan. 3, 2018, 3 pgs.
Canadian Intellectual Property Office, Office Action for Canadian Patent Application No. 2961224 dated Nov. 28, 2017, 4 pgs.
PTO, Notice of the Reason for Refusal for Japanese Patent Application No. 2017-515791 dated Aug. 15, 2017, 1 pg.
Korean International Patent Office, Office Action for Korean Application No. 10-2017-7010542 dated Jun. 23, 2017, 10 pgs.
Protest to Canadian Patent Application No. 2961224 filed Oct. 24, 2017, 3 pgs.
European Patent Office, Notice of Third Party Observations regarding Patent Application No. 157748019-1358 dated Nov. 7, 2017, 20 pgs.
Anonymous, Third Party Observations regarding Great Britain Patent Application No. 1705340.6 dated Nov. 2, 2017, 36 pgs.
Cheigh et al., "Intense pulsed light (IPL) and UV-C treatments for inactivating Listeria monocytogenees on solid medium and seafoods", Food Research International 54, Nov. 2013, pp. 745-752.
Abida et al., "Pulsed Light Technology: a novel method for food preservation"; International Food Research Journal, 21(3), 2014, pp. 839-848.
Wekhof et al., "Pulsed UV Disintegration (PUVD): a new sterilisation mechanism for packaging and broad medical-hospital applications", The First International Conference on Ultraviolet Technologies, Washington DC, Jun. 14-16, 2001, 15 pgs.
Helman, "How a new machine uses UV rays to blast killer bacteria", Forbes Magazine (online), Nov. 2, 2011, 3 pgs.
Steris Corporation, Pathogen UV Disinfection System—SD970, Nov. 1, 2013, 8 pgs.
TRU-D SmartUVC, "Vancouver General First Hospital in Canada to use TRU-D SmartUVC Superbug Killing Robot", Feb. 1, 2013, 3 pgs.
Bohrerova et al., "Comparative disinfection efficiency of pulsed and continuous-wave UV irradiation technologies", Water Research 42, Jun. 2008, pp. 2975-2982.
Deal et al., "Alterations of Bacteria Colony Counts in the Inanimate Environment of an Intensive Care Unit by Use of the Tru-D Device," UV Solutions NW, Bellevue, Washington, link labeled "Tru-D Bacteria Trial (203KB PDF)" from http://www.uvsolutionsnw.com/ultraviolet-effectivenessresearch.html, Apr. 15, 2002 to Aug. 1, 2002, 8 pages.
Elmnasser et al., "Pulsed-light system as a novel food decontamination technology: a review" Canadian Journal of Microbiology 53, Aug. 1, 2007, pp. 813-821.
Kowalski et al., "A Specular Model for UVGI Air Disinfection Systems", IUVA News, The Pennsylvania State University, Mar. 2005, pp. 19-26.
Kowalski et al., "UVGI Design Basics for Air and Surface Disinfection", HPAC Engineering Jan. 2000, pp. 100-110.
Luksiene et al., "High-power pulsed light for microbial decontamination of some fruits and vegetables with different surfaces", Journal of Food, Agriculture & Environment, vol. 10 (3&4), Jul.-Oct. 2012, pp. 162-167.
Mahida et al., First UK evaluation of an automated ultraviolet-C room decontamination device (Tru-D0, Journal of Hospital Infection, Aug. 1, 2013, 4 pgs.

Memarzadeh et al., "Applications of ultraviolet germicidal irradiation disinfection in health care facilities: Effective adjunct, but not stand-alone technology", Association for Professionals in Infection Control and Epidemiology, Inc., Jun. 2010, pp. S13-S24.
Perkinelmer Optoelectronics, "High Performance Flash and Arc Lamps Catalog", not dated, pp. 1-39.
Rice et al., "Examination of Peak Power Dependence in the UV Inactivation of Bacterial Spores", Applied and Environmental Microbiology, Dec. 2001, pp. 5830-5832.
Sanitas Company, "Tru-D (Total-Room Ultraviolet Disinfector) product overview" downloaded from internet on Jun. 13, 2014, publication date unknown, 2 pgs.
Shaefer et al., "Pulsed UV lamp performance and comparison with UV mercury lamps", Journal of Environmental Engineering ad Science, May 1, 2007, pp. 303-310.
Steriliz , "RD Disinfector Product Manual", 2014, 97pgs.
Steriliz, "Clostridium difficile Sport inactivation Study Using Ultraviolet-C Energy", May 2012, 10 pgs.
Turtoi et al., "Ultraviolet light efficacy for microbial inactivation on fruit juices, nectars and apple cider", Journal of Agroalimentary Processes and Technologies 2013 pp. 130-138.
Umezawa et al., "A Comparative Study of the Bactericidal Activity and Daily Disinfection Housekeeping Surfaces by a New Portable Pulsed UV Radiation Device", Curr Microbial 64, Mar. 25, 2012, pp. 581-587.
Wekhof, "Disinfection with Flash Lamps", PDA Journal of Pharmaceutical Science & Technology vol. 54, No. 3 May/Jun. 2000, pp. 264-276.
Otaki et al, "Inactivation differences of microorganisms by low pressure UV and pulsed xenon lamps" Water Science and Technology vol. 47, pp. 185-190, Feb. 2003.
Wang et al., "Pulsed ultra-violet inactivation spectrum of *Escherichia coli*", Water Research vol. 39, pp. 2921-2925, Jul. 5, 2005.
Verrotti et al., "Human photosensitivity: from pathophysiology to treatment", European Journal of Neurology vol. 12 Issue 11, Oct. 20, 2005, pp. 828-841.
Wengraitis et al., "Pulsed UV-C disinfection of *Escherichia coli* with light emitting diodes, emitted at various repetition rates and duty cycles", Photochemistry Photobiology vol. 89, Oct. 1, 2012, pp. 127-131.
Owens et al., High-Dose Ultraviolet C Light Inactivates Spores of Bacillus Atrophaeus and Bacillus Anthracis Sterne on Nonreflective Surfaces:, Applied Biosafety, vol. 10(4), Nov. 4, 2005, pp. 240-247.
Steribeam, "Comparison between Continuous and Pulsed UV Sources", Product information from SteriBeam Systems GmbH, date unknown, 3 pgs.
Stibich et al., "Evaluation of a Pulsed-Xenon Ultraviolet Room Disinfection Device for Impact on Hospital operation and Microbial Reduction", Infection Control and Hospital Epidemiology vol. 32 No. 3, Mar. 2011, 3pgs.
Murdoch et al., "Bactericidal Effects of 405 nm Light Exposure Demonstrated by Inactivation of *Escherichia, Salmonella, Shigella, Listeria* and *Mycobacterium* Species in Liquid Suspensions and on Exposed Surfaces", Scientific World Journal 2012 Article 137805, 9 pgs.
Murdoch et al., "Lethal effects of high-intensity violet 405-nm light on *Saccharamyces cervisiae*, Candid albicans, and on dormant and geminating spores of Aswergillus niger", Fungal Biology 117 (2013), pp. 519-527.
MRSA-UV LLC, "Turbo-UV Portable Room Sanitizer" brochure, 2012, 2pgs.
Patent Office, "Notice of Allowance" for Japanese Patent Application No. 2017-515791 dated Feb. 6, 2018, 2pgs.
KIPO, "Notice of Allowance" for Korean Patent Application No. 10-2017-7010542 dated Jan. 29, 2018, 2 pgs.
Federal Service on Intellectual Property, Search report for Russian Patent Application No. 2017113071 dated Dec. 6, 2017, 2pgs.
Patent Office, Office Notification for Russian Patent Application No. 2017113071/15 dated Dec. 27, 2017, 5 pgs.
European Patent Office, Office Action for European Patent Application No. 15 774 803.9 dated Jan. 25, 2018, 5 pgs.

(56) References Cited

OTHER PUBLICATIONS

Coufal et al., "Evaluation of a Method of Ultraviolet Light Sanitation of Broiler Hatching Eggs", 2003 Poultry Science vol. 82, May 1, 2003, pp. 754-759.
Federal Service for Intellectual Property, Decision to Grant for Russian Patent Application No. 2017113071/15 dated May 25, 2018, 17 pages.
Canadian Intellectual Property Office, Notice of Allowance for Canadian Patent Application No. 2961224 dated Jun. 12, 2018, 1 page.
International Searching Authority, International Search Report and Written Opinion for Application PCT/US2015/051010, dated Nov. 2, 2015, 10 pgs.
International Preliminary Examining Authority, Written Opinion of the International Preliminary Examining Authority for Application PCT/US2015/051010, dated Sep. 5, 2016, 7 pgs.
International Preliminary Examining Authority, Notification of Transmittal of the international Preliminary Report on Patentability for Application PCT/US2015/051010, dated Dec. 16, 2016, 8 pgs.
Patents Directorate United Kingdom, Examination Report dated Mar. 28, 2018 for Application GB1705340.6, 3 pages.
European Patent Office, Office Action for European Patent Application No. 15774803.9 dated Aug. 29, 2018, 5 pages.
Patents Directorate, Notification of Grant for UK Patent Application No. GB2545375 dated Sep. 11, 2018, 2 pages.
Patents Directorate, Extended Search Report and Written Opinion for European Patent Application No. 18152537.9 dated Apr. 30, 2018, 7 pages.
United States Patent and Trademark Office, Office Action for U.S. Appl. No. 15/454,158 dated Jul. 13, 2018, 9 pages.

* cited by examiner

ROOM AND AREA DISINFECTION UTILIZING PULSED LIGHT WITH MODULATED POWER FLUX AND LIGHT SYSTEMS WITH VISIBLE LIGHT COMPENSATION BETWEEN PULSES

PRIORITY CLAIM

This application is a divisional of pending U.S. patent application Ser. No. 15/454,158 filed Mar. 9, 2017, which is a continuation of International Patent Application No. PCT/US2015/051010 filed Sep. 18, 2015, which designates the United States and claims priority to U.S. Provisional Patent Application No. 62/052,036, filed Sep. 18, 2014.

BACKGROUND OF THE INVENTION

1. Field of the Invention

This invention generally relates to light disinfection systems and methods and, more specifically to, room and area disinfection systems and methods utilizing pulsed light with modulated power flux and light systems with visible light compensation between pulses.

2. Description of the Related Art

The following descriptions and examples are not admitted to be prior art by virtue of their inclusion within this section.

Pulsed light sources are used in a variety of applications to generate recurrent pulses of ultraviolet (UV) light. Examples of applications include but are not limited to polymer curing, food sterilization, fluid and object disinfection, and room/area decontamination. Area/room disinfection, in particular, is increasingly becoming an application of interest as pulsed UV light as been shown to significantly reduce the number of pathogenic microorganisms in an area/room in a short period of time. In particular, pulsed UV light has been shown to deactivate and, in some cases, kill microorganisms on objects and surfaces in a room/area at distances within approximately 3 meters from a UV light source, depending on factors such as reflectivity and complexity of objects in the room. In addition, pulsed UV light has been shown to reduce the number of pathogenic microorganisms within a room/area to a level considered much less harmful to human health in less than approximately 5 minutes. Examples of area/room disinfection applications are those used in hospitals and those used in agricultural operations, such as for breeding and/or farming animals.

Many studies suggest germicidal efficacy for microorganism deactivation is chiefly due to the dose of ultraviolet electromagnetic radiation subtype C (UVC) light applied as well as efficacy in the ultraviolet electromagnetic radiation subtype B (UVB), or the dose of energy within the wavelengths of 200 and 320 nanometers. This efficacy is determined by measuring quantum yield or the number of germicidal actions taking place per incident photon arriving on a microorganism. Conventional uses of pulsed UV light for UV sanitation of foods generally rely on a high level of power per pulse to maximize UVC dose, specifically such that the UV light may penetrate into crevices or pores of a food's surface. UV curing and sintering processes also utilize a relatively high level of power per pulse to maximize UV dose. In other applications which utilize pulsed UV light to deactivate microorganisms, such as wastewater disinfection, a relatively low pulse power may be used but at a relatively high frequency in order to maximize UVC dose for a given period of time. In particular, it is known that pulse power and pulse frequency each have an effect on UVC dose (however not necessarily a proportional effect), but have an inverse relationship relative to each other (i.e., the higher the power per pulse, the lower the pulse frequency and vice versa) and, thus, each can be varied depending on the needs of the application.

Area/room disinfection applications utilizing pulse UV light, however, induce limitations to which pulse power and pulse frequency may be optimized. In particular, area/room disinfection processes differ from other pulsed UV light processes (e.g., curing, sintering, food sanitization and wastewater treatment processes) in that the UV light must be transmitted a relatively long distance (e.g., up to 3 meters from a UV source). Due to the inverse-square law, conventional area/room disinfection applications utilizing pulsed UV light are generally limited to using a relatively high level of power per pulse to insure a sufficient dose of UVC is transmitted across a room/area. In order to maximize the UVC dose generated, conventional area/room disinfection applications utilizing pulse UV light use a relatively low pulse frequency (e.g., less than approximately 2 Hz). Despite the compromise of a relatively low pulse frequency, an area/room disinfection device utilizing pulse UV light may be limited in the power level it can generate for a pulse due to size limitations of the device. In particular, it is often preferred for area/room disinfection devices to be readily portable such that they may be moved to multiple rooms of a building and, thus, the size of the pulsed lamp and the power supply used to operate it may be limited. Other applications of pulsed UV applications (e.g., curing, sintering, food sanitization and wastewater treatment processes) are generally not designed for portability and, thus, are often not limited to the amount of UV light it can generate.

Furthermore, conventional area/room disinfection applications utilizing pulse UV light are generally limited to frequencies less than 2 Hz to the keep the pulse frequency from potentially inducing seizures (the range of which is generally considered to be 3-60 Hz). In particular, although area/room disinfection utilizing pulsed UV light is typically performed by an automated device in a vacated room/area to limit or prevent exposure of UV light, some rooms/areas may not block the visible light generated from the disinfection device. In order to limit exposure of the intensity and/or pulse rate of pulsed light, provisions are often used to shield transmission of visible light from the room/area, such as blocking windows of a room or shielding gaps at the top and/or bottom of a room divider. Such shielding provisions, however, may not block all light from all areas/rooms and, thus, the pulse frequency of an area/room disinfection device utilizing pulsed UV light may generally be less limited to 2 Hz or less for safety considerations.

In view of the general knowledge of germicidal efficacy of pulsed UV light being chiefly dependent on overall UVC dose and the aforementioned restrictions of area/room disinfection devices which use pulse UV light, the efficiency and efficacy of conventional area/room disinfection devices utilizing pulse UV light have been limited. Accordingly, it would be beneficial to develop methods and systems for increasing the efficiency and efficacy of area/room disinfection devices utilizing pulse UV light.

SUMMARY OF THE INVENTION

The following description of various embodiments of apparatuses is not to be construed in any way as limiting the subject matter of the appended claims.

Embodiments of a method for reducing bacterial contamination on surfaces in an enclosed space which is suitable for human occupancy includes generating pulses of light at a frequency greater than approximately 20 Hz from a germicidal light source of a disinfection apparatus that is arranged in the enclosed space and projecting the pulses of light to surfaces in the enclosed space at least 1.0 meter from the disinfection apparatus. The pulses of light generated by the germicidal light source comprise a pulse duration and an energy flux sufficient to generate a power flux between approximately 200 W/m$^2$ and approximately 5000 W/m$^2$ of ultraviolet light in the wavelength range between 200 nm and 320 nm at the surfaces. An embodiment of an apparatus for performing such a method includes a germicidal light source arranged within the apparatus such that germicidal light generated from the germicidal light source is projected exterior to the apparatus. The apparatus further includes circuitry configured to generate pulses of light from the germicidal light source at a frequency greater than approximately 20 Hz.

Other embodiments of a method for disinfecting surfaces includes generating pulses of light from a germicidal light source, wherein the pulses of light from the germicidal light source comprise germicidal light and visible light and generating pulses of light from a visible light source that is distinct from the germicidal light source. The projections of visible light from the visible light source and projections of visible light from the germicidal light source produce a continuous stream of visible light or a collective stream of visible light pulsed at a frequency greater than 60 Hz. An embodiment of a disinfection apparatus for performing such a method includes a germicidal light source configured to emit germicidal light and visible light and pulse circuitry configured to generate pulses of light from the germicidal light source at a set frequency. The apparatus further includes a visible light lamp distinct from the germicidal pulsed light source and additional circuitry configured to cause the visible light lamp to generate light.

BRIEF DESCRIPTION OF THE DRAWINGS

Other objects and advantages of the invention will become apparent upon reading the following detailed description and upon reference to the accompanying drawings in which.

Figure 1:
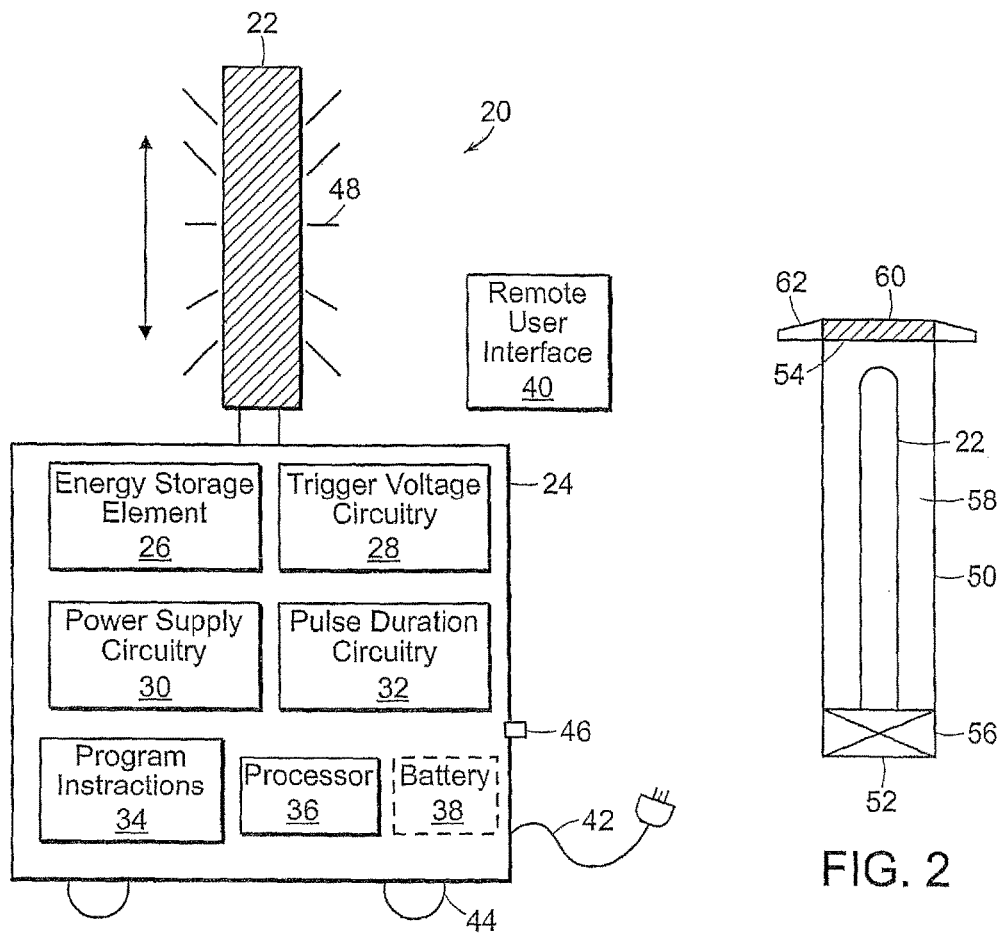
FIG. 1 illustrates an example of a room/area disinfection device.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

Methods and apparatuses for disinfecting surfaces are provided which generate pulses of light from germicidal light sources at a frequency of greater than approximately 3 Hz. In particular, methods and apparatuses are provided which generate pulses of ultraviolet light at a frequency greater than approximately 20 Hz with significantly lower power flux than pulses of light generated from conventional disinfection apparatuses. Such methods and apparatuses are described in more detail below in reference to FIGS. 1-7. In addition, methods and apparatuses are provided which generate pulses of light including ultraviolet light and visible light from one lamp at a frequency between approximately 3 Hz and approximately 60 Hz and further emit visible light from a separate lamp to insure visible light emitted by the two lamps produces a continuous stream of visible light or a collective stream of visible light pulsed at a frequency greater than 50 Hz. Such methods and apparatuses are described in more detail below in reference to FIGS. 8 and 9. As will be set forth in more detail below, the apparatuses and components described herein are not limited to the depictions in the drawings. Several other configurations of apparatuses and components may be considered. Furthermore, it is noted that the drawings are not necessarily drawn to scale.

Each of the methods and apparatuses described herein includes use of a germicidal light source. The term "germicidal light source" as used herein refers to a light source designed to generate and emit germicidal light, i.e., light which is capable of deactivating or killing microorganisms, particularly disease carrying and/or disease producing microorganisms (a.k.a., germs). The term "kill," as used herein, means to cause the death of an organism. The term "deactivate," as used herein, means to render an organism unable to reproduce without killing. The germicidal light sources considered for the methods and apparatuses described herein may be configured to generate any type of germicidal light. Ranges of light which are known to be germicidal include ultraviolet light between approximately 200 nm and approximately 320 nm and visible violet-blue light (also known as high-intensity narrow-spectrum (HINS) light) between approximately 400 nm and approximately 470 nm. Examples of germicidal light sources which may be configured to generate ultraviolet light and/or HINS light include discharge lamps, light emitting diode (LED) solid state devices, and excimer lasers. HINS lamps are generally constructed of LEDs. In some cases, the germicidal light sources considered for the methods and apparatuses described herein may be polychromatic in that they generate light of more than one wavelength. In some further embodiments, the germicidal light sources considered for the methods and apparatuses described herein may generate light which is not germicidal, such as but not limited to visible light, but such capability will not deter from the reference of the light sources being germicidal.

In any case, the germicidal light sources considered for the apparatuses described herein may be of any size and shape, depending on the design specifications of the apparatuses. Lamps having exterior surfaces between approximately 50 cm$^2$ and approximately 250 cm$^2$ may be particularly appropriate for the methods and apparatuses described herein since they are directed to room/area disinfection processes, but lamps with smaller or larger exterior surfaces may be used.

As noted above, the methods and apparatuses described herein generate recurrent pulses of light from germicidal light sources at frequencies greater than approximately 3 Hz. As such, the methods and apparatus described herein include configurations by which to generate pulses of light from germicidal light sources. For example, the methods and apparatuses described herein may utilize a pulsed germicidal light source and applicable circuitry for triggering a stored amount of electrical energy for a set pulse duration to the pulsed germicidal light source. An example of an apparatus with such a configuration of components is described in more detail below in reference to FIG. 1. The term "pulsed germicidal light source" as used herein refers to a lamp which is designed to only generate and emit recurrent pulses of germicidal light (i.e., it cannot generate and emit continuous streams of germicidal light). Such lamps differ from "continuous germicidal light sources" which are configured to generate and emit continuous streams of germicidal light upon application of continuous current thereto. In some cases, the methods and apparatuses described herein may utilize a continuous germicidal light source and applicable circuitry for turning the continuous germicidal light source on and off at a set frequency such that the continuous germicidal light source may generate and emit recurrent pulses of germicidal light. An example of an apparatus with such a configuration of components is described in more detail below in reference to FIG. 3. To accommodate both types of light sources for the methods and apparatuses described herein, the methods and apparatuses described herein may be referred to as methods, apparatuses, devices or systems which generate recurrent pulses of germicidal light.

As noted above, examples of germicidal light sources which may be configured to generate ultraviolet light and/or HINS light include discharge lamps. A discharge lamp as used herein refers to a lamp that generates light by means of an internal electrical discharge between electrodes in a gas. The term encompasses gas-discharge lamps, which generate light by sending an electrical discharge through an ionized gas (i.e., a plasma). The term also encompasses surface-discharge lamps, which generate light by sending an electrical discharge along a surface of a dielectric substrate in the presence of a gas, producing a plasma along the substrate's surface. As such, the discharge lamps which may be considered for the germicidal light sources described herein may include gas-discharge lamps as well as surface-discharge lamps. Discharge lamps may be further characterized by the type of gas/es employed and the pressure at which they are operated. The discharge lamps which may be considered for the methods and apparatuses described herein include those of low pressure, medium pressure and high intensity. In addition, the gas/es employed may include helium, neon, argon, krypton, xenon, nitrogen, oxygen, hydrogen, water vapor, carbon dioxide, mercury vapor, sodium vapor and any combination thereof. In some embodiments, various additives and/or other substances may be included in the gas/es. In any case, the discharge lamps considered for the germicidal sources described herein may include those which generate continuous light and those which generate recurrent pulses of light, the latter of which are often referred to as flashtubes or flashlamps.

A commonly used gas-discharge lamp used to produce continuous light is a mercury-vapor lamp, which may be considered for some of the germicidal sources described herein. It emits a strong peak of light at 253.7 nm, which is considered particularly applicable for germicidal disinfection and, thus, is commonly referenced for ultraviolet germicidal irradiation (UVGI). A commonly used flashlamp which may be considered for the disinfection apparatuses described herein is a xenon flashtube. A xenon flashtube generates a broad spectrum of light from ultraviolet to infrared (including visible light) and, thus, provides ultraviolet light in the entire spectrum known to the germicidal (i.e., between approximately 200 nm and approximately 320 nm). In addition, a xenon flashtube can provide relatively sufficient intensity at wavelength ranges known to be optimally germicidal (i.e., between approximately 229 nm and approximately 231 nm and between approximately 260 nm and approximately 265 nm). Moreover, a xenon flashtube generates an extreme amount of heat, which can further contribute to the deactivation and killing of microorganisms.

As noted above, a surface-discharge lamp may also be considered for some of the disinfection apparatuses described herein. Similar to a xenon flashtube, a surface-discharge lamp produces ultraviolet light in the entire spectrum known to the germicidal (i.e., between approximately 200 nm and approximately 320 nm). In contrast, however, surface-discharge lamps operate at higher energy levels per pulse and, thus, greater UV efficiency, as well as offer longer lamp life as compared to xenon flashtubes. It is noted that the aforementioned descriptions and comparisons of a mercury-vapor lamp, a xenon flashlamp and a surface discharge lamp in no way restrict the disinfection apparatuses described herein to include such lamps. Rather, the aforementioned descriptions and comparisons are merely provided to offer factors which one skilled in the art may contemplate when selecting a discharge lamp for a disinfection apparatus, particularly depending on the objective and application of the apparatus.

Turning to the drawings, FIG. 1 illustrates an example of an apparatus configured to generate pulses of ultraviolet light at frequencies greater than approximately 20 Hz with significantly lower power flux relative to pulses of light generated from conventional disinfection apparatuses. In particular, FIG. 1 shows apparatus 20 with base 24 with a number of components to affect such functionalities for germicidal pulsed light source 22, the specifics of which will be described in more detail below. More specifically, FIG. 1 illustrates base 24 including energy storage element/s 26, trigger voltage circuitry 28, power circuitry 30, pulse duration circuitry 32, program instructions 34, processor 36, and optional battery 38. As further shown in FIG. 1, apparatus 20 may include additional components, such as remote user interface 40, power cord 42, wheels 44 and occupancy sensor 46. It is noted that placement of the noted components are not restricted to the depiction of FIG. 1, but rather the components may be disposed at any location to affect the functionality they impart to apparatus 20. As such, the components shown in base 24 in FIG. 1 need not be disposed within base 24 necessarily. Furthermore, power cord 42, wheels 44 and occupancy sensor 46 may be disposed at other locations of apparatus 20. In any case, apparatus 20 may include additional or alternative components that are not shown in FIG. 1, such as but not limited to a user interface on the apparatus (in addition or alternative to remote user interface 40), a handle to aid in portability of the apparatus, a power socket inlet (in addition or alternative to power cord 42) and/or additional sensors, such as additional occupancy sensors and light sensors.

Regardless of their location within apparatus 20, the electrical components of apparatus 20 are in general in electrical communication with each other via wired and/or wireless connections to affect operations of the apparatus. For instance, power circuitry 30 is electrically coupled to energy storage element/s 26, trigger voltage circuitry 28, and pulse duration circuitry 32 to generate a pulse of light from germicidal pulsed light source 22 and power circuitry 30 is further electrically coupled to processor 36, remote user interface 40 (and/or a user interface on the apparatus), and occupancy sensor 46 to affect the commencement and termination of operations of the apparatus. In addition, processor 36 is electrically coupled to program instructions 34 such that the program instructions may be executed by the processor and, in addition, processor 30 is electrically coupled to remote user interface 40 (and/or a user interface on the apparatus) and/or any sensors of apparatus 20 to affect operations of germicidal pulsed light source 22 in accordance with program instructions 34. Other electrical connections may be included in the apparatus 20 between any of the noted components and other components of apparatus 20 to affect operations thereof.

As noted above, apparatus 20 includes a number of components in base 24 to affect the generation pulsed light from pulsed germicidal light source 22 at a frequency greater than approximately 20 Hz with significantly lower power flux relative to pulses of light generated from conventional disinfection apparatuses. In particular, base 24 includes trigger voltage circuitry 28 which is configured to apply a sufficient voltage at a set frequency by which to activate pulsed germicidal light source 22 to generate recurrent pulses of light. In addition, base 24 includes energy storage element/s 26 and pulse duration circuitry 32 respectively configured to discharge a set amount of stored energy in a set amount of time to pulsed germicidal light source 22. The components making up trigger voltage circuitry 28, energy storage element/s 26 and pulse duration circuitry 32 and the operation incurred by such features will generally depend on design of the germicidal light source. For example, a flashlamp includes one or more capacitors for energy storage element/s and includes one or more inductors for its pulse duration circuitry 32. In addition, the trigger voltage in a flashlamp serves to ionize the gas in the flashlamp and cause the capacitor/s to discharge their accumulated energy thereto for the duration governed by the inductor/s. In any case, the voltage levels applied to trigger voltage circuitry 28 and pulse duration circuitry 32 as well as to energy storage element/s 26 to accumulate charge therein may generally depend on the design specifications (e.g., the desired pulse frequency, pulse duration, pulse intensity, exterior surface area of pulsed germicidal light source 22, among other parameters known to those skilled in the art of pulsed light source design). Example ranges are described in reference to FIG. 6 regarding the desired power fluxes shown therein.

As noted above, apparatus 20 configured to generate pulses of ultraviolet light at frequencies greater than approximately 20 Hz. Such functionality is governed by trigger voltage circuitry 28. In particular, trigger voltage circuitry 28 may be configured to apply a trigger voltage at a frequency greater than 20 Hz to germicidal pulsed light source 22 and, in some applications, frequencies greater than 40 Hz, greater than 50 Hz or even greater than 55 Hz may be particularly suitable. In other embodiments, trigger voltage circuitry 28 may be configured to apply a trigger voltage at a frequency greater than 60 Hz and, particularly between approximately 60 Hz and approximately 100 Hz to germicidal pulsed light source 22. In particular, it may be advantageous for trigger voltage circuitry 28 to apply a trigger voltage to germicidal pulsed light source 22 at a frequency above the safety threshold for inducing seizures (which is generally considered to be about 60 Hz). In yet further embodiments, it may be advantageous for trigger voltage circuitry 28 to apply a trigger voltage to germicidal pulsed light source 22 at a frequency slightly above the seizure inducing threshold for safety purposes (e.g., in light of variability of voltage draw from a mains alternating current power supply of a building), such as a frequency of 65 Hz or greater.

In some cases, it may be advantageous for trigger voltage circuitry 28 to apply a trigger voltage to germicidal pulsed light source 22 at a frequency at which light appears to be continuous to the human eye. For example, light pulsed at frequencies of 60 Hz and greater wherein the pulse durations are approximately 25 microseconds appears to be continuous to the human eye. It is believed that the minimum frequency level to invoke the appearance of continuous light to the human eye varies with the duration of the pulses, specifically the minimum frequency level increases when pulse durations decrease and vice versa. Thus, the frequency level to set a trigger voltage at to induce the appearance of continuous light to the human eye may vary among applications, depending on the design specifications of the germicidal pulsed light source, particularly the pulse duration. In yet further embodiments, a frequency range of 60 Hz to 90 Hz may be beneficial for maximizing UVC dose from a germicidal pulsed light source within a given period without causing excessive operational stress on the discharge lamp. It is noted that for the development of the ideas provided herein, trigger voltages of 67 Hz were repeatedly tested, but the scope of the ideas disclosed herein should not be limited to such a frequency. Other exemplary ranges of frequencies greater than 20 Hz may be considered, including those which exceed 100 Hz.

As noted above, apparatus 20 may include optional battery 38 connected to the power supply circuitry, which may be used for supplying power to one or more components of the apparatus. It is noted, however, given their large power requirements, it is generally advantageous to power germicidal pulsed light source 22, energy storage elements 26, trigger voltage circuitry 28 and pulse duration circuitry 32 from a mains alternating current power supply of a building in which the apparatus is arranged via a power cord comprising the apparatus or connected to a power socket inlet of the apparatus. In such cases, the power supply circuitry may include a step-up transformer for increasing alternating current received via the power cord and/or the power socket inlet and further a rectifier for converting alternating current received from the step-up transformer into direct current for operation of the germicidal pulsed light source. It is contemplated, however, that continuous germicidal light sources of some apparatus may be powered by a battery since they have much lower power requirements. In such cases, it may be possible for the apparatus to be void of a power cord and/or a power socket inlet for connecting to a mains alternating current power supply of a building.

Figure 2:
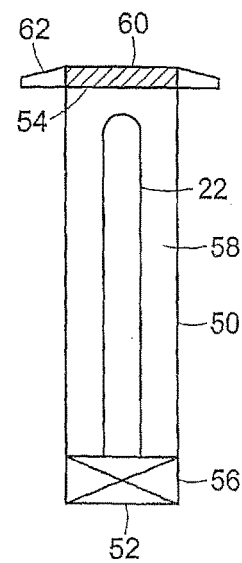
FIG. 2 illustrates an example of a cooling system which may be used for the light sources of the apparatuses disclosed herein.

In some cases, pulsed germicidal light sources may generate a lot heat and, thus, may need to be cooled during operation. The type of cooling system may include convection cooling, forced air/gas cooling or liquid cooling, the selection of which may generally depend on the design characteristics of the apparatus, particularly the power flux it is configured to generate. An example of a forced air system is illustrated in FIG. 2 as an example for pulsed germicidal light source 22 in FIG. 1. In particular, FIG. 2 illustrates pulsed germicidal light source 22 disposed within circumjacent barrier 50 between air inlet 52 and air outlet 54 with air inlet 52 having an air moving device 56 disposed in proximity thereto, in effect forming plenum 58 around pulsed germicidal light source 22. Circumjacent barrier 50 is made of a material transparent to the germicidal light such that germicidal light generated by pulsed germicidal light source 22 may be transmitted exterior to apparatus 20.

In some embodiments, circumjacent barrier 50 may include a material which attenuates some or all visible light generated by pulsed germicidal light source 22 and or apparatus may include additional circumjacent barrier of such material surrounding circumjacent barrier 50. The inclusion of such a material in either of such cases may be beneficial when the intensity of visible light generated by pulsed germicidal light source 22 is very high, particularly when it is causes visual discomfort or distraction upon exposure. In other cases, however, when the intensity of visible light generated by pulsed germicidal light source 22 is relatively low, it may be advantageous to omit barrier around pulsed germicidal light source 22 that attenuates visible light. In particular, a visible light filter could reduce the intensity of light in other ranges, such as a germicidal range and, thus, reduce the power flux of the germicidal light emitted from apparatus 20.

In any case, air moving device 56 draws air into plenum 58 through air inlet 52 and discharges through air outlet 54. In an alternative embodiment, air moving device 56 may be arranged in proximity to air outlet 54. In any case, air moving device 56 may be any device configured to cause air to flow, including but not limited to a fan or a turbine. In cases in which a turbine is used in the apparatuses described herein, the turbine may be used to supply power to one or more components of the apparatuses, including any of the components described herein or a battery of the apparatus. In any case, air inlet 52 may include a filter to remove particular matter from an incoming air stream.

In some cases, air outlet 54 may include an ozone reducing device 60, such as a carbon filter or a device which produces free radicals catalysts that covert ozone to diatomic oxygen. In particular, ozone may, in some cases, be created as a byproduct from the use of pulsed germicidal light source 22, specifically if the lamp generates ultraviolet light of wavelengths shorter than approximately 240 nm since such a spectrum of UV light causes oxygen atoms of oxygen molecules to dissociate, starting the ozone generation process. Ozone is a known health and air quality hazard and, thus, the release of it by devices is regulated. It is also known that ozone is an effective germicidal agent and deodorizer and, thus, if the amount of ozone to be generated by pulsed germicidal light source 22 is lower than the local/regional exposure limits for ozone, it may be beneficial to exclude an ozone reducing device 60 from air outlet 56. In yet other cases, air outlet 56 may have a portion with an ozone reducing device and a portion without an ozone reducing device and further an air flow regulator to respectively route air through the different portions depending on operating parameters and/or modes of disinfection processes employed by apparatus 20. Examples of air outlets having such features are described in more detail in U.S. application Ser. No. 14/790,827 filed Jul. 2, 2015, which is incorporated herein by reference as if set forth fully herein.

Regardless of whether apparatus 20 includes an ozone reducing device, apparatus 20 may, in some cases, include reflector at an elevation above pulsed germicidal light source 22 to redirect light emitted from pulsed germicidal light source 22 downwardly. In particular, the methods and apparatuses described herein may be particularly specific to room/area disinfection and, thus, it may be advantageous to include a reflector for redirecting light from pulsed germicidal light source 22 to a region exterior to the apparatus 20 and which is between approximately 2 feet and approximately 4 feet from a floor of a room in which apparatus 20 is arranged. In general, the region between approximately 2 feet and approximately 4 feet from a floor of a room is considered a "high touch" region of a room since objects of frequent use are generally placed in such a region. Examples of objects typically found in a high touch zone of a room include but are not limited to desktops, keyboards, telephones, chairs, door and cabinet handles, light switches and sinks. Examples of objects in high touch zones of hospital rooms additionally or alternatively include beds, bedside tables, tray tables and intravenous stands. Due to such a region being considered a high touch zone, it is generally considered the area of highest probability to come in contact with germs and some studies indicate that the high touch zone may be the area having the highest concentration of germs.

FIG. 2 illustrates an example of a reflector for apparatus 20 disposed at an elevation above pulsed germicidal light source 22 for redirecting light emitted from the light source downwardly to a region which is between approximately 2 feet and approximately 4 feet from a floor of a room in which apparatus 20 is arranged, specifically annular reflector 62 around air outlet 54. Other configurations (e.g., size, shape, angle, distance from pulsed germicidal light source 22) of reflectors may be used and/or reflectors may be arranged at other locations within apparatus 20 to aid in distributing light to areas of interest in a room, particularly distances 1 to 3 meters away from apparatus 20. Examples of area/room disinfection apparatuses having reflectors with such function are disclosed in U.S. application Ser. No. 13/706,926 filed Dec. 6, 2012 and Ser. No. 13/708,208 filed Dec. 7, 2012 as well as International Patent Application No. PCT/US2014/059698 filed Oct. 8, 2014, all of which are incorporated herein by reference as if set forth fully herein.

Another configuration which characterizes the apparatuses described herein to specifically affect room/area disinfection is that the germicidal light source arranged within the apparatus such that germicidal light generated from the germicidal light source is projected exterior to the apparatus. In some cases, a germicidal light source may be arranged lengthwise substantially perpendicular to a horizontal plane of a support structure supporting one end of the light source. In addition or alternatively, the apparatus may be void of an opaque component 360° around an elongated portion of the germicidal light source such that light emitted from the germicidal light source encircles the apparatus, such as shown for pulsed germicidal light source 22 in FIGS. 1 and 22. Furthermore, some of apparatuses described herein may include an actuator for moving its germicidal light source within the apparatus (such as with respect to a support structure supporting the light source) to aid in the distribution of light in a room or area. In such regard, the methods described herein may include automatically moving a germicidal light source within apparatus while the germicidal light source is emitting light and/or in between pulses of light. Another feature which characterizes the apparatuses described herein to specifically affect room/area disinfection is have an occupancy sensor, such as a motion sensor, a thermal sensor or a photo recognition sensor. In such cases, the methods described herein may include inhibiting and/or terminating the generation of pulses of light from the germicidal light source upon making a detection which is indicative of occupancy within the area/room in which the apparatus is arranged.

Yet other features which may be included in the apparatuses described herein to specifically affect room/area disinfection are those that affect portability of the apparatus, such as wheels and/or a handle. In particular, is often preferred for area/room disinfection devices to be readily portable such that they may be moved to multiple rooms of a building. In some embodiments, the apparatuses described herein may include processor executable program instructions for receiving data regarding characteristics of an enclosed space in which the disinfection apparatus is to be operated. In general, the phrase "characteristics of an enclosed space" as used herein refers to physical attributes as well as non-physical attributes of an enclosed space. Non-physical attributes of an enclosed space include but are not necessarily limited to identifiers used to reference an enclosed space (e.g., room number and/or room name) and occupancy information regarding an enclosed space (e.g., infection information of a patient previously occupying the space or a patient scheduled to occupy the space). Physical attributes of an enclosed space include but are not necessarily limited to size and/or dimensions of the enclosed space and/or the number, size, distances, locations, reflectivity and/or identification of surfaces, objects and/or items within the enclosed space. In some cases, a physical attribute of an enclosed space may be the identification of one or more pathological organisms and, sometimes further the number or concentration of such organism/s in the enclosed space, in a particular region of the enclosed space, or on a particular surface in the enclosed space.

In any case, the data received regarding the characteristics of the enclosed space in which the disinfection apparatus is to be operated may be utilized in a number of manners, including but not limited to recordation or reporting purposes or setting one or more operational parameters of the apparatus. In some embodiments, the apparatuses described herein may include a means for automatically moving the apparatus. In some such cases, the apparatus may include program instructions to move the apparatus along a predetermined route. In addition or alternatively the apparatus may include program instructions to move the apparatus in accordance with room characteristics of a room which have been analyzed via one or more sensors of the apparatus, including sensors for mapping or modeling an area/room. Examples of area/room disinfection apparatuses with some of the aforementioned program instructions are disclosed in U.S. application Ser. No. 13/706,926 filed Dec. 6, 2012, which is incorporated by reference as if set forth fully herein.

Other configurations which may aid in facilitating the apparatuses for room/area disinfection may be considered. More specifically, the apparatuses described herein may be configured (with the configurations noted above or with other configurations) to expose areas and rooms as well as objects as a whole to germicidal light and, thus, may be specifically configured to distribute light in a spacious manner to an ambient of a room in which the disinfection apparatus is arranged. In addition, the apparatuses described herein may be configured to distribute germicidal light to surfaces within a room or area that are greater than 1 meter or even 2 or 3 meters from a germicidal flashlamp. The apparatuses may be of any shape, size, or configuration in which to achieve such objectives. Examples of area/room disinfection apparatuses are disclosed in U.S. application Ser. No. 13/706,926 filed Dec. 6, 2012 and Ser. No. 13/708,208 filed Dec. 7, 2012; as well as International Patent Application No. PCT/US2014/059698 filed Oct. 8, 2014, all of which are incorporated herein by reference as if set forth fully herein. Other configurations of area/room disinfection apparatuses, however, may be employed for apparatuses described herein.

As used herein, the term "room/area disinfection" refers to the cleansing of a space which is suitable for human occupancy so as to deactivate, destroy or prevent the growth of disease-carrying microorganisms in the area. The phrase "a space which is suitable for human occupancy" as used herein refers to a space in which an adult human being of average size may comfortably occupy for at least a period of time to eat, sleep, work, lounge, partake in an activity, or complete a task therein. In some cases, spaces suitable for human occupancy may be bounded and include a door for entering and exiting the room. In other cases, a space suitable for human occupancy may be an area with indeterminate boundaries. Examples of spaces which are suitable for human occupancy include but are not limited to single patient rooms, multiple occupancy patient rooms, bathrooms, walk-in closets, hallways, bedrooms, offices, operating rooms, patient examination rooms, waiting and/or lounging areas and nursing stations. As used herein, the term "enclosed space" refers to an area having its boundaries defined by barriers blocking a vast majority or all germicidal light transmission exterior to the area.

Figure 4:
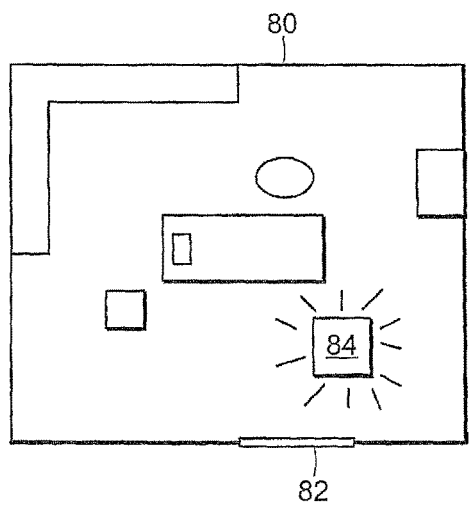
FIGS. 4 and 5 illustrates examples of enclosed spaces.
Figure 5:
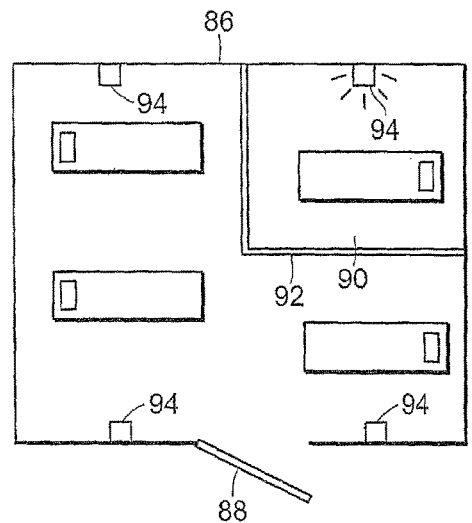

Examples of enclosed spaces suitable for human occupancy in which the apparatuses described herein may be used to conduct area/room disinfection processes are shown in FIGS. 4 and 5. In particular, FIG. 4 illustrates operating or patient room 80 having door 82 closed and having disinfection apparatus 84 disposed therein. In such cases, the walls and windows (if applicable) of room 80 as well as door 82 serve as barriers defining the boundaries of room 80 to form an enclosed space suitable for human occupancy. Although door 82 is shut to consider the space enclosed, germicidal light may be transmitted around the periphery of the door if it is not sealed. In such cases, a vast majority of germicidal light transmission is blocked from being transmitted exterior to room 80 and, thus, is considered an enclosed space.

FIG. 5, on the other hand, illustrates multi-occupancy room 86 having door 88 open but including partitioned area 90 sectioned off by room divider 92, such as a cubicle curtain. As shown, partitioned area 90 includes one of the plurality of disinfection apparatus 94. In such cases, the walls and windows (if applicable) of room 86 in partitioned area 90 as well as room divider 92 serve as barriers defining the boundaries of partitioned area 90 to form an enclosed space suitable for human occupancy. It is appreciated that room divider 92 may not fully extend to the walls, ceiling, and/or the floor of room 86 and, thus, germicidal light may be transmitted around room divider 92. In such cases, a vast majority of germicidal light transmission is blocked from being transmitted exterior to partitioned area 90 and, thus, is considered an enclosed space. In general, disinfection apparatuses 84 and 94 shown in FIGS. 4 and 5 may include any of the apparatuses disclosed herein. It is noted that the number, size, placement, and portability of disinfection apparatuses 84 and 94 are not exclusive to the respective embodiments of FIGS. 4 and 5 showing a room as enclosed space and a partitioned section of a room as an enclosed space. In particular, any of the apparatuses disclosed herein may be employed in any enclosed space which is suitable for human occupancy.

Figure 3:
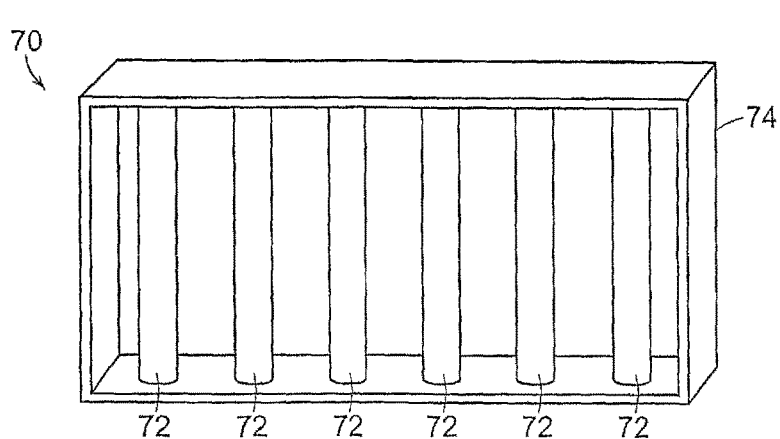
FIG. 3 illustrates an example of a different room/area disinfection device.

As noted above, apparatus 20 in FIG. 1 is an example of an apparatus which may be used to generate pulses of ultraviolet light at frequencies greater than approximately 20 Hz with significantly lower power flux relative to pulses of light generated from conventional disinfection apparatuses. Several other configurations of apparatuses may be considered for such functionalities, one of which is depicted in FIG. 3. In particular, FIG. 3 illustrates apparatus 70 including a plurality of germicidal light sources 72 arranged in frame 74. In some cases, the backside of apparatus 70 may include a backside panel spanning the areal dimension of frame 74 to prevent emission of germicide from the backside of apparatus 70. In other embodiments, the backside of apparatus 70 may be open such that light may be emitted on either side of the apparatus. In any case, apparatus 70 may be considered for use for area/room disinfection. In some embodiments, apparatus 70 may be mountable on a wall or a ceiling. Alternatively, apparatus 70 may be a standalone device.

In any case, the dimensions and shape of frame 74 may vary from that depicted in FIG. 3. More specifically, frame 74 is not limited to being rectangular and/or having the relatively thin sidewalls depicted in FIG. 3. Furthermore, the orientation of apparatus 70 is not limited to its longitudinal dimension being horizontal. Moreover, apparatus 70 is not limited to having multiple cylindrical germicidal light sources orientated in the manner shown in FIG. 3. Rather, apparatus 70 may include any number, size, shape and orientation of germicidal light sources. Moreover, germicidal light sources 72 may include the same type of germicidal light source or different types of germicidal light sources. In some cases, apparatus 70 may be configured to move one or more of germicidal sources 72 to extend out of frame 74 to enhance distribution of germicide/s generated therefrom into an ambient of the apparatus. An example configuration to offer such an option may include retractable tracks extending out from frame 74 in alignment with germicidal sources 72, along which the germicidal sources may be moved manually or by an actuator.

In any case, apparatus 70 may include any of the features described in reference to apparatus 20 of FIG. 1. In particular, apparatus 70 may include one or more of energy storage element/s 26, trigger voltage circuitry 28, power circuitry 30, pulse duration circuitry 32, program instructions 34, processor 36, optional battery 38, remote user interface 40, power cord 42, wheels 44, occupancy sensor 46, a user interface on the apparatus (in addition or alternative to remote user interface 40), a handle to aid in portability of the apparatus, a power socket inlet (in addition or alternative to power cord 42) and/or additional sensors, such as additional occupancy sensors and light sensors. Such features are not shown in apparatus 70 to simplify the drawing in FIG. 3. Furthermore, such features are not described in reference to apparatus 70 for the sake of brevity.

Furthermore, apparatus 70 may include any of the cooling system features described in reference to apparatus 20 of FIG. 1 and the specific embodiment of the forced air cooling system described in reference to FIG. 2. For example, although not shown, apparatus 70 may include any number of air moving devices, air inlets, and air outlets. In addition, the front side and possibly the back side of apparatus 70 may include panels within frame 74 which are transparent to ultraviolet light and, if desired, also opaque to visible light. In general, the air moving device/s, air inlet/s, and air outlet/s may be arranged within any side of frame 74. In addition or alternatively, air moving device/s may be arranged internal to frame 74, particularly but not necessarily in alignment with air inlet/s or air outlet/s within the frame. In any case, air moving device/s may be arranged upstream or downstream of an air stream induced through frame 44. In some cases, apparatus 70 may include an air moving device disposed at one end of at least one of germicidal sources 72 (and, in some cases, include an air moving device disposed at the end of each of germicidal sources 72) to induce an air stream which flows substantially parallel with the longitudinal dimension of the germicidal light sources, such as described for germicidal source 22 in reference to FIG. 2. In other cases, apparatus 70 may have air moving devices arranged to induce an air stream that traverses germicidal sources 72.

As noted above, however, the apparatuses described herein may include several different configurations and, thus, apparatus 70 may, in some cases, include different features than apparatus 20 of FIG. 1. For example, germicidal light sources 72 may not be pulsed germicidal light sources, but rather continuous germicidal light sources and, thus, apparatus 70 may not include energy storage element/s 26, trigger voltage circuitry 28, and pulse duration circuitry 32. Instead, apparatus 70 may include circuitry for turning the continuous germicidal light sources on and off at a set frequency (e.g., >20 Hz) such that the continuous germicidal light sources may generate and emit recurrent pulses of germicidal light.

As noted above, FIGS. 1 and 3 depict examples of apparatuses configured to generate pulses of ultraviolet light at frequencies greater than approximately 20 Hz with significantly lower power flux relative to pulses of light generated from conventional disinfection apparatuses. The term "power flux", as used herein, refers to the transmission rate of radiant energy at a given surface per unit area. Synonymous terms for power flux include "irradiance", "power density" and "radiation intensity" and, thus, the terms may be used interchangeably herein. The term "energy flux", as used herein, refers to the amount of radiant energy at a given surface per unit area. A synonymous term for energy flux is "radiant energy" and, thus, the terms may be used interchangeably herein.

As noted above, many studies suggest germicidal efficacy for microorganism deactivation is chiefly due to the dose of ultraviolet electromagnetic radiation subtype C (UVC) light applied, or the dose of energy within the wavelengths of 200 and 320 nanometers. In light thereof, studies directed to analyzing energy requirements for germicidal efficacy generally focus on the power flux or energy flux of ultraviolet light and, in some cases, the power flux or energy flux of UVC. In particular, some studies teach that a minimum power flux of ultraviolet radiation is needed to achieve sufficient germicidal efficacy. Other studies teach additional parameters need to be met in addition to power flux, such as particular ratios of peak, average and root mean square power of ultraviolet radiation and/or a contrived relationship correlating energy discharged to the lamp, surface area of the lamp and pulse duration. Yet other studies tie in pulse frequency requirements in addition to power flux, such as specifying a minimum pulse frequency or a required range of pulse frequency.

For example, U.S. Pat. No. 6,264,802 to Kamrukov et al. teaches applying UV radiation to liquids, air and surfaces with a radiation intensity of at least 100 KW/m$^2$, a pulse duration between 1 and 1000 microseconds and further that the energy discharged to the lamp, surface area of the lamp and the pulse duration follow a specified relationship. The patent is silent with regard to what pulse frequencies may be employed. U.S. Pat. No. 5,144,146 to Wekhof teaches different power requirements for purifying wastewater in that an average power density of UV needs to be maintained at a value of at least 100 W/m² within the wastewater while the UV source is pulsed at frequency of 5 to 100 Hz. It is noted that the teaching of maintaining an average power density of UV at a value of at least 100 W/m² is in reference to the entire operation cycle of the lamp rather than just when UV radiation is delivered from the lamp, which differs from the other power requirement parameters disclosed in the patent. In particular, U.S. Pat. No. 5,144,146 to Wekhof further teaches that the ratio of root mean square power to average power delivered by the UV source needs to be in range of 10:1 to 100:1 and the ratio of peak power to average power delivered by the UV source needs to be in the range of 1000:1 to 10,000:1.

As will be described in more detail below, the area/room disinfection processes described herein do not meet any of these prior art requirements, specifically that processes are conducted with significantly lower power fluxes at distances 1.0 meter and farther from the disinfection apparatuses. In particular, it was discovered during the development of the ideas provided herein that sufficient germicidal efficacy could be obtained with pulses of light generated at frequencies greater than approximately 50 Hz and with relatively low power flux, particularly less than 5000 W/m² of UV light in the wavelength range of 200 nm to 320 nm at surfaces at least 1.0 meter from the disinfection apparatuses. As used herein, sufficient germicidal efficacy refers to a 2-log or more reduction in bacterial contamination on surfaces.

Figure 7:
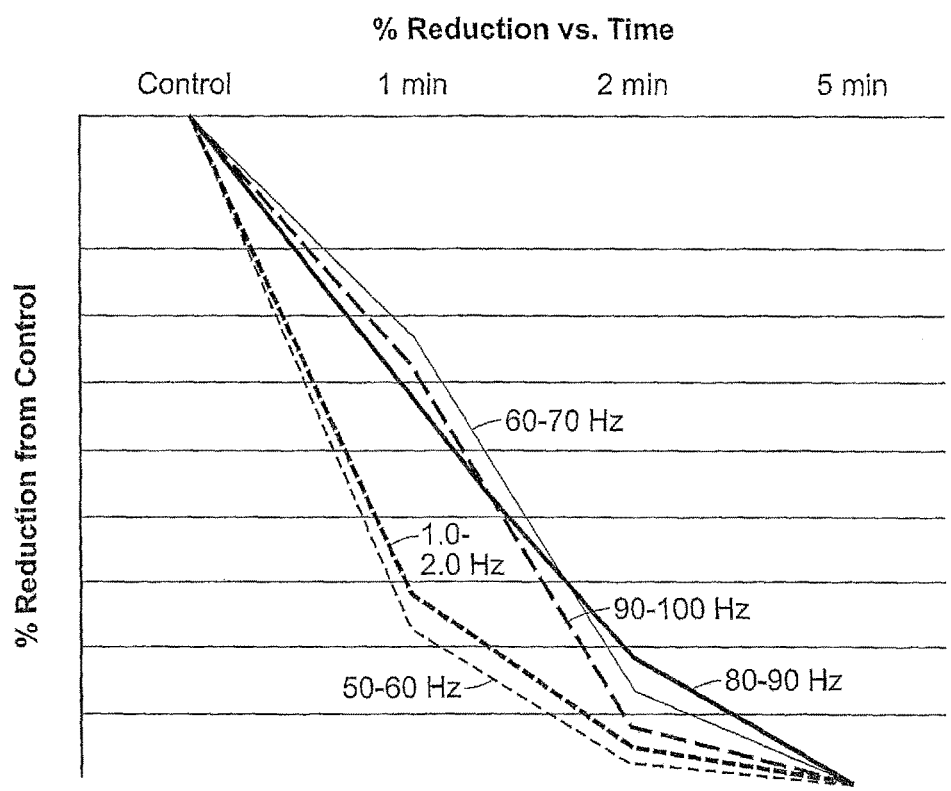
FIG. 7 illustrates a graph showing disinfection efficacy of five different trigger voltage frequencies over time at a surface approximately 2 meters away from a germicidal pulsed light source.

More specifically, in development of the ideas provided herein, disinfection efficacies of five different frequencies ranging between 1.0 Hz and 100 Hz were evaluated at a surface 2.0 meters away from a germicidal pulsed light source, the results of which are depicted in FIG. 7. The lamps used for each of the frequencies were xenon flashlamps constructed of the same materials, the same surface area and the same fill pressure. In the interest to evaluate any variances induced by the differences in frequencies, the cycle times of the disinfection processes for each of the frequencies was the same (i.e., 5 minutes) and the lamps were conducted at operational parameters that produced comparable power flux at the lamp surface over that cycle time (i.e., all light generated at the lamp, not just UV or UVC). To accommodate such a power flux, the pulse duration and the amount of energy accumulated at the capacitor/s for discharge to the lamps for the disinfection processes conducted at higher frequencies are generally lower than disinfection processes conducted at lower frequencies. In making such adjustments, the higher frequency processes are conducted with a lower power flux per pulse than the lower frequency processes. In other words, the transmission rate of radiant energy at a given surface per unit area is less for each pulse.

As shown in FIG. 7, disinfection efficacy is substantially similar among the five different trigger voltage frequencies for 5 minute disinfection processes. Based on the data obtained for the 5 different frequencies tested, it is apparent that a disinfection process may be modulated by the varying the amount, duration and frequency of UV light applied to a surface at a given distance without substantially affecting the disinfection efficacy. More specifically, it has been found that UV light may be applied at a lower intensity and shorter pulse duration but at a higher frequency at a surface at a given distance for a given cycle time and yield substantially similar germicidal efficacy as compared to processes applying higher intensity of UV light at lower doses. Several theories are contemplated to explain such findings. One theory involves keeping the targeted pathogen in a "shocked state," in which there is a potential for damage. In particular, it is theorized that the longer the pathogen is in a "shocked state," which is caused by incident photons, the more likely the cell is to be deactivated. In order to acquire this state, it is believed that there is a minimum level intensity of UV light needed, which based on the data obtained was attainable with at least 100 Hz frequencies. In the interest of efficiency, it is speculated that higher frequencies of pulsing minimize the amount of photons to reach this state, but simultaneously maximize the number of "shock state" events.

A second theory involves overwhelming enzymatic cellular repair mechanisms that aid in photo-repair (i.e., repairing a previously deactivated cell). In particular, more frequent photon flux induced by higher frequency applications could overwhelm cellular repair mechanisms before repair can be completed. It is further contemplated that these theories can be interrelated, specifically that the tested disinfection efficacy of the higher frequencies could involve a combination of the two. Furthermore, it is conceivable that these theories and/or the results found in testing the five different aforementioned frequencies could be limited to inanimate objects and/or nosocomial pathogens.

Moreover, it is speculated that the comparable disinfection efficacies achieved among the five different pulse frequencies tested with respect to FIG. 7 may be due to an increase in power flux at specific wavelengths that potentially have a higher degree of germicidal effect relative to other wavelengths in the UVC range as pulse frequency is increased. In particular, it was discovered during the development of the ideas provided herein that a disinfection process that generates pulsed light between 60 Hz and approximately 70 Hz produces greater power flux at wavelengths of approximately 230 nm, approximately 248 nm and approximately 261 nm than a disinfection process that generates pulsed light between 1.0 Hz and 2.0 Hz, despite the overall power flux in the UVC range of the 60-70 Hz disinfection process being lower than the power flux generated in the UVC range of the 1.0-2.0 Hz disinfection process. It theorized that the larger peaks at approximately 230 nm, approximately 248 nm and approximately 261 nm may compensate for the overall lower power flux in the UVC range relative to the 1.0-2.0 Hz process lending to comparable disinfection efficacy.

Moreover, it is speculated that the comparable disinfection efficacies achieved among the five different pulse frequencies tested with respect to FIG. 7 may be due to larger variations of power flux in germicidal ranges of light as pulse frequency is increased. In particular, it was discovered during the development of the ideas provided herein that a disinfection process that generates pulsed light between 60 Hz and 70 Hz produces a larger variation of power flux in the UVC range, specifically between 210 nm and 320 nm and, more specifically between approximately 225 nm and approximately 265 nm, than a disinfection process that generates pulsed light between 1.0 Hz and 2.0 Hz. It theorized that the larger variation of power flux may compensate for the overall lower power flux in the UVC range relative to the 1.0-2.0 Hz process lending to comparable disinfection efficacy. In particular, a larger variation of power flux within a spectrum of radiation correlates to atomic line radiation, which generally corresponds to bound-bound energy state transitions of the photons. In contrast, a smaller variation of power flux within a spectrum of radiation correlates to continuum radiation, which generally corresponds to free-bound and free-free energy state transitions of the photons. In general, photons in bound-bound energy state transitions have a higher amount of energy than photons in free-bound and free-free energy state transitions. It is theorized that the higher energy of photons induced by a larger power flux variations exhibited in the UVC range for the 60-70 Hz disinfection process may compensate for the overall lower power flux in the UVC range relative to the 1.0-2.0 Hz process, lending to comparable disinfection efficacy between the two processes.

Some of the variation of power flux in the UVC range for the 60-70 Hz disinfection process is due to the large peaks centered at approximately 230 nm, approximately 248 nm and approximately 261 nm. In taking integral of such peaks relative to the integral of the range between approximately 225 nm and approximately 265 nm, an approximation of the degree of variation across such a range was quantified. In particular, approximately 60% of the power flux in that range was due to the peaks for the 60-70 Hz process and approximately 50% of the power flux in that range is due to the peaks for the 1.0-2.0 Hz process. It is noted that the 60-70 Hz process exhibited larger power flux variations across other wavelength ranges of the ultraviolet spectrum and it is contemplated those variations may further contribute to the relatively comparable disinfection efficacy of the 60-70 Hz process relative to the 1.0-2.0 Hz process despite the overall lower power flux in the UVC range for the 60-70 Hz process. Moreover, the 60-70 Hz process exhibited a larger variation of power fluxes of visible violet-blue light between approximately 420 nm and approximately 470 nm than the power flux variation for the 1.0-2.0 Hz process in the same range and it is contemplated those larger power flux variations may contribute to the relatively comparable disinfection efficacy of the 60-70 Hz process relative to the 1.0 Hz process. In particular, visible violet-blue light between approximately 400 nm and approximately 470 nm is known to be germicidal and, thus, the higher variation of power flux in such a region may aid in germicidal efficacy.

Given the discovery that comparable disinfection efficacies may be obtained at 2.0 meters away from a pulsed light source conducted at pulse frequencies ranging between 1.0 Hz and 100 Hz, it is contemplated that a room/area disinfection apparatus can be operated at any pulse frequency if the parameters of the operation are governed to generate a set power flux of light at the lamp which is known to affect sufficient germicidal efficacy at a desired distance from the disinfection apparatus. It is further contemplated that a room/area disinfection apparatus can be operated at any pulse frequency if a desired power flux of UVC radiation is known to affect sufficient germicidal efficacy at a desired distance from the disinfection apparatus. In particular, the operational parameters of the apparatus, such as pulse duration, energy discharged to the lamp and lamp itself (particularly the exterior surface of the lamp) may be optimized to achieve the desired power flux of UVC radiation at the desired pulse frequency.

Figure 6:
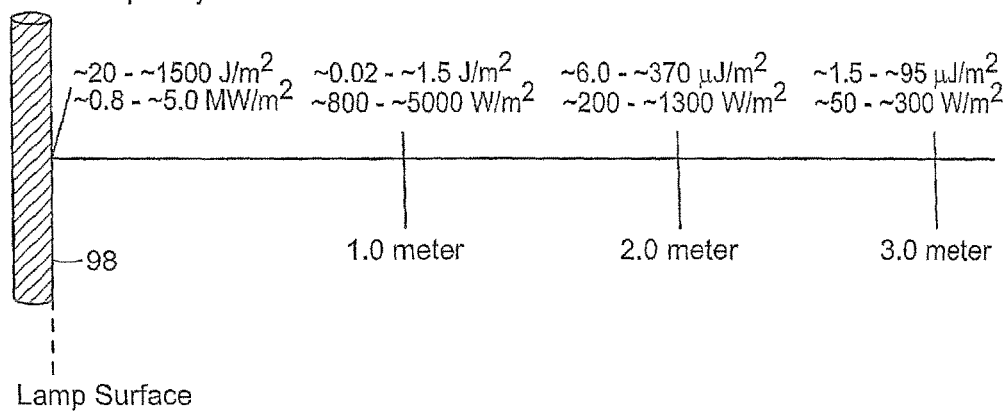
FIG. 6 illustrates target ranges of energy flux and power flux of ultraviolet light between approximately 200 nm and approximately 320 nm for a lamp surface and distances 1.0, 2.0 and 3.0 meters away from the lamp.

The disclosure provided herein focuses on ranges of power fluxes of ultraviolet light between approximately 200 nm and approximately 320 nm during a given pulse which may be used for area/room disinfection apparatuses operated at frequencies greater than approximately 20 Hz, particularly for sufficient germicidal efficacy at 1.0, 2.0 and 3.0 meters away from the apparatus. In particular, FIG. 6 illustrates germicidal light source 98 of a room/area disinfection apparatus with target ranges of energy flux and power flux of ultraviolet light between approximately 200 nm and approximately 320 nm specified for the lamp surface and distances 1.0, 2.0 and 3.0 meters away from the apparatus. The entire room/area disinfection apparatus is not shown in FIG. 6 to simplify the drawing, but the apparatus may generally include any of apparatus features and configurations described in reference to FIGS. 1-3. It is particularly noted that germicidal light source 98 may be a pulsed germicidal light source or may be a continuous germicidal light source, wherein the latter embodiment, the room/area disinfection apparatus includes circuitry to turn the light source on and off to pulse light therefrom.

As shown in FIG. 6, target ranges of energy flux of ultraviolet light between approximately 200 nm and approximately 320 nm at the surface of germicidal light source 98 may be between approximately 20 J/m$^2$ and approximately 1500 J/m$^2$. In addition, the target range of power flux of ultraviolet light between approximately 200 nm and approximately 320 nm at the surface of germicidal light source 98 may be between approximately 0.8 MW/m$^2$ and approximately 5.0 MW/m$^2$. In more specific embodiments, the energy flux and power flux of ultraviolet light between approximately 200 nm and approximately 320 nm at the surface of germicidal light source 98 may be between approximately 20 J/m$^2$ and approximately 500 J/m$^2$ and between approximately 0.8 MW/m$^2$ and approximately 1.5 MW/m$^2$, respectively. As further shown in FIG. 6, target ranges of energy flux of ultraviolet light between approximately 200 nm and approximately 320 nm approximately 1.0 meter from germicidal light source 98 may be between approximately 0.02 J/m$^2$ and approximately 1.5 J/m$^2$. In addition, the target range of power flux of ultraviolet light between approximately 200 nm and approximately 320 nm approximately 1.0 meter away germicidal light source 98 may be between approximately 800 W/m$^2$ and approximately 5000 W/m$^2$. In more specific embodiments, the energy flux and power flux of ultraviolet light between approximately 200 nm and approximately 320 nm approximately 1.0 meter from germicidal light source 98 may be between approximately 0.02 J/m$^2$ and approximately 0.5 J/m$^2$ and between approximately 800 W/m$^2$ and approximately 1500 W/m$^2$, respectively.

FIG. 6 further shows target ranges of energy flux of ultraviolet light between approximately 200 nm and approximately 320 nm approximately 2.0 meter from germicidal light source 98 may be between approximately 6.0 μJ/m$^2$ and approximately 370 μJ/m$^2$. In addition, the target range of power flux of ultraviolet light between approximately 200 nm and approximately 320 nm approximately 2.0 meters from germicidal light source 98 may be between approximately 200 W/m$^2$ and approximately 1300 W/m$^2$. In more specific embodiments, the energy flux and power flux of ultraviolet light between approximately 200 nm and approximately 320 nm approximately 2.0 meters from germicidal light source 98 may be between approximately 6.0 μJ/m$^2$ and approximately 250 μJ/m$^2$ and between approximately 200 W/m$^2$ and approximately 800 W/m$^2$, respectively. Moreover, FIG. 6 further shows target ranges of energy flux of ultraviolet light between approximately 200 nm and approximately 320 nm approximately 3.0 meters from germicidal light source 98 may be between approximately 1.5 μJ/m$^2$ and approximately 95 μJ/m$^2$. In addition, the target range of power flux of ultraviolet light between approximately 200 nm and approximately 320 nm approximately 3.0 meters from germicidal light source 98 may be between approximately 50 W/m$^2$ and approximately 300 W/m$^2$. In more specific embodiments, the energy flux and power flux of ultraviolet light between approximately 200 nm and approximately 320 nm approximately 3.0 meters from germicidal light source 98 may be between approximately 6.0 µJ/m$^2$ and approximately 120 µJ/m$^2$ and between approximately 200 W/m$^2$ and approximately 600 W/m$^2$, respectively.

As noted above, the area/room disinfection processes described herein do not meet any of parameters requirements taught in U.S. Pat. No. 6,264,802 to Kamrukov et al., U.S. Pat. No. 5,144,146 to Wekhof, U.S. Application No. US 2008/0150443 to Tipton for operation of germicidal pulsed light sources. In particular, the maximum power flux recited in reference to FIG. 6 for distances 1.0, 2.0 and 3.0 meters from a germicidal light source is 5000 W/m$^2$, which is two orders of magnitude lower than the 100 KW/m$^2$ minimum power flux requirement taught in U.S. Pat. No. 6,264,802 to Kamrukov et al. Likewise, the average power density of UV light over a cycle time of a disinfection process that is conducted using any of the target power flux ranges noted in FIG. 6 is likely at least two orders of magnitude less than the requirement taught in U.S. Pat. No. 5,144,146 to Wekhof. In particular, a disinfection process conducted with a pulse frequency between 60 Hz and approximately 70 Hz for the development of the ideas provided herein was calculated to have an average power flux in the UV range over the operation of the disinfection process of 2.9 W/m$^2$, which is two orders of magnitude lower than the 100 W/m$^2$ minimum power flux requirement taught in U.S. Pat. No. 5,144,146 to Wekhof. Furthermore, any disinfection process conducted using any of the target power flux ranges noted in FIG. 6 likely does not meet the ratio of root mean square (RMS) power to average power requirement or the ratio of peak power to average power requirement. For example, a disinfection process conducted with a pulse frequency between 60 and 70 Hz for the development of the ideas herein exhibited a ratio of RMS power to average power of 1.4 and a ratio of peak power to average power of 4.2 approximately 1.0 meter from the germicidal light source during a given pulse.

For some embodiments, frequencies in the range of 55 Hz to 80 Hz and, particularly 67 Hz, were deemed particularly suitable for the disinfection processes described herein. In particular, frequencies of these values have a higher power per pulse than higher frequencies, and, thus, overall UVC dose of the noted frequencies is greater and UVC dose is substantially greater at larger distances due to the inverse square law. Furthermore, conversion of electrical energy to optical energy at the frequencies of the noted range is more efficient than higher frequencies. Moreover, there is less overall loss of energy at the frequencies of the noted range when dealing with relatively large angles of incidence and reflection. For room disinfection processes, it is desirable to maximize the manipulation of light to reach areas that are not in line of sight of the disinfection source. Although frequencies in the range of 55 Hz to 80 Hz may be advantageous for several reasons, it is reasonable to consider frequencies greater than 80 Hz or lower than 55 Hz for the disinfection processes described herein.

Furthermore, frequencies of 50 Hz and greater exhibited beneficial characteristics distinct from the processes conducted at a frequency between 1.0 Hz and 2.0 Hz. In particular, the noise of the light generated from frequencies of 50 Hz and greater was substantially less than the noise of light generated from the 1.0-2.0 Hz frequency. Furthermore, the visual intensity of the light generated from frequencies of 50 Hz and greater was substantially less than the intensity of light generated from the 1.0-2.0 Hz frequency. Further to such a regard, it was found in additional testing that the visual intensity of the light generated from frequencies of 50 Hz and greater was also substantially less than the intensity of light generated from the 1.0-2.0 Hz frequency when a visible light filter was used to block visible light emitted from the lamp for the 1.0-2.0 frequency process (and no filter was used on the apparatus for the frequencies of 50 Hz and greater).

Additionally in such testing, it was found that the disinfection efficacy of a 5 minute cycle time for the 1.0-2.0 Hz frequency process employing a visible light filter decreased substantially, notably over half a log difference, relative to embodiments in which a visible light filter was not used on the disinfection apparatus during a 1.0-2.0 Hz process. It is believed the decrease in disinfection efficacy was due to a combination of altered spectra of light radiation emitted as well as a decrease in the total UVC dose at the targeted surface. Given a visible light filter is generally needed for 1.0-2.0 frequency disinfection processes due to the extreme of visible light generated, there is the possibility for shorter disinfection cycles (i.e., shorter than 5 minutes) for disinfection processes using frequencies of 50 Hz and greater since a visible light filter may not be needed to attenuate visual stimuli. Also, an improvement in bulb life may be realized for disinfection processes using frequencies of 50 Hz and greater due to the lower power flux per pulse employed.

As noted above, it may be advantageous utilize a frequency above the safety threshold for inducing seizures (which is generally considered to be about 60 Hz) for the methods and apparatuses described herein, but as further noted above, lower frequencies (i.e., frequencies less than 60 Hz) may be employed. More specifically, frequencies considered to potentially induce seizures (the range of which is generally considered to be 3-60 Hz) may be employed within the methods and apparatuses disclosed herein. In such cases, provisions may be used to shield or mask the generation of visible light from the germicidal light source. For example, the disinfection apparatus may include an optical filter configured to attenuate a majority or all visible light generated from the germicidal light source. In addition or alternatively, the disinfection apparatus may include a visible light source distinct from the germicidal light source that is used to either mask the visible light generated by the germicidal light source or is synchronously pulsed with pulses of light from the germicidal light source such that the collective projection of visible light from the two light sources is greater than a safety threshold for inducing seizures (such as greater than 60 Hz).

Figure 8:
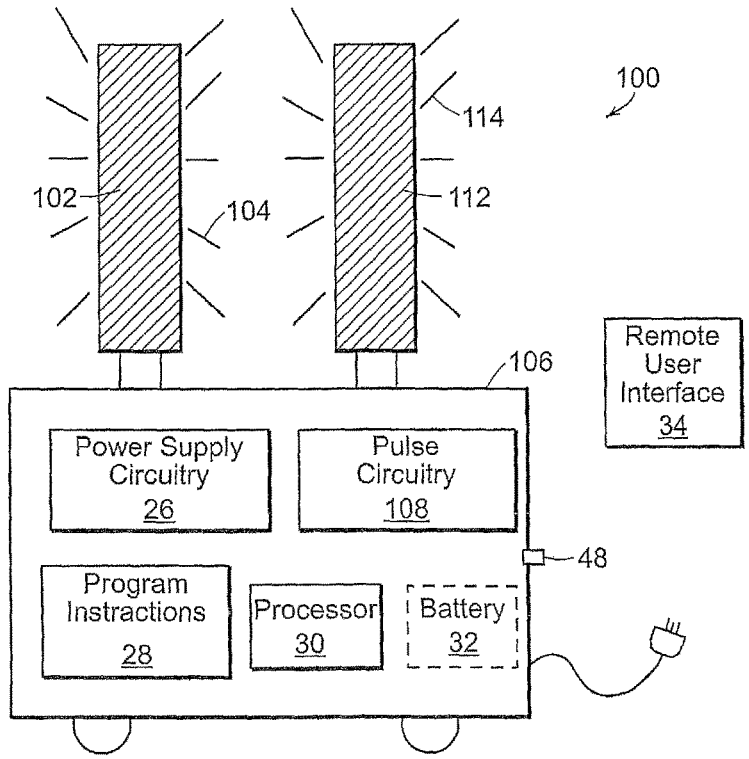
FIG. 8 illustrates an example of an apparatus having a germicidal light source and a separate visible light source.

FIG. 8 illustrates an example of an apparatus including a germicidal light source and a separate visible light source which may be used in such a manner. In particular, FIG. 8 illustrates apparatus 100 including germicidal light source 102 and visible light source 112. Germicidal light source 102 may include any germicidal light source 102 which is configured to generate both germicidal light and visible light. For example, germicidal light source 102 may be configured to generate germicidal ultraviolet light and visible light. In addition or alternatively, germicidal light source 102 may be configured to generate germicidal visible violet-blue light. In any case, germicidal light source 102 may be pulsed germicidal light source or may be a continuous germicidal light source. In the latter case, apparatus 100 may include circuitry for turning the continuous germicidal light source on and off at a set frequency such that recurrent pulses of light may be generated from the continuous germicidal light source.

Visible light source 112 may include any light source 102 which is configured to generate visible light, including those which can produce continuous light and those which produced pulsed light. In some cases, visible light source 112 may additionally generate light which is not visible. In particular embodiments, visible light source 112 may additionally generate germicidal light, such as germicidal ultraviolet light and germicidal visible violet-blue light. In some of such cases, visible light source 112 may generate the same type of light as germicidal light source 102 and, in further embodiments, may be a light source of similar type as germicidal light source 102 (i.e., the light sources generate light in the same manner). In yet other cases, however, visible light source 112 may not be configured to generate germicidal light. Examples of visible light lamps which may be considered include but are not limited to LED lamps, fluorescent lamps and any type of germicidal light source that produces visible light.

In any case, the visible light generated by visible light source 112 may have an average intensity of at least approximately 90% of the average visible light intensity projected from the germicidal light source 102 or passed through an optical filter surrounding germicidal light source 102, if applicable. In some embodiments, the visible light generated by visible light source 112 may have greater intensity than the visible light intensity projected from germicidal light source 102 or passed through an optical filter surrounding germicidal light source 102, if applicable. For example, in embodiments in which visible light source 112 emits continuous light, the intensity of the visible light generated by visible light source 112 may be at least approximately 150% greater than the intensity of the visible light projected from germicidal light source 102 or passed through an optical filter surrounding the germicidal light source, if applicable. Alternatively, in embodiments in which visible light source 112 generates pulses of visible light, the visible light generated by visible light source 112 may have an average intensity between approximately 90% and approximately 110% of the average visible light intensity projected from germicidal light source 102 or passed through an optical filter surrounding the germicidal light source, if applicable. In general, such intensities may be measured at any given distance from light sources, but it may be particularly suitable if the noted intensities are measured at a given distance 1.0 meter or greater from the light sources and, in some cases, at distances 2.0 meters or greater or even 3.0 meters or greater from the light sources. In this manner, the projection of visible light from visible light source 112 may be sufficient to mask or be substantially equivalent (i.e., +/−10%) to the projection of visible light from germicidal light source 102.

In some particular cases, visible light source 112 may include similar dimensional configurations (i.e., shape and size) as germicidal light source 102. For example, it may be advantageous to for visible light source 112 and germicidal light source 102 to have exterior surface areas within approximately 20% of each other. Having such comparable surface areas may facilitate the light sources to emit a comparable amount of light in addition to the light being of comparable intensity. In some cases, visible light source 112 and germicidal light source 102 may have exterior surface areas within approximately 10% of each other or less. In particular embodiments, visible light source 112 and germicidal light source 102 may have approximately the same exterior surface areas.

In some cases, visible light lamp 112 may be tinted to match the spectrum of visible light generated from the germicidal light source 102. In addition or alternatively, it may be advantageous for visible light source 112 to be a lamp which uses less power than the germicidal light source 102. In particular, a disinfection process utilizing such a visible light lamp and also utilizing a germicidal light source pulsed at a frequency which light appears to be pulsed to the human eye (e.g., at frequencies less than 60 Hz) may require less power consumption as compared to a disinfection process using a germicidal light source pulsed at a frequency which light appears to be continuous to the human eye. Such lower power consumption may be an incentive to use the dual lamp process versus a process only utilizing a germicidal light source.

Although not necessarily so limited, apparatus 100 may be a room/area disinfection apparatus and, thus, germicidal light source 102 and visible light source 112 may be configured to distribute light in a spacious manner to an ambient of an area/room in which apparatus 100 is arranged. In addition, germicidal light source 102 and visible light source 112 may be configured within the apparatuses described herein to distribute light to surfaces within a room or area that are greater than 1.0 meter or even 2.0 or 3.0 meters from apparatus 100. In specific embodiments, germicidal light source 102 and visible light source 112 may be configured to have a substantially similar spacial light dispersement patterns. The light sources may be of any shape, size, or configuration in which to achieve such objectives. In specific embodiments, germicidal light source 10 and visible light source 112 may each be arranged lengthwise perpendicular to a horizontal plane of a support structure of an apparatus as shown in FIG. 8.

Other features which may facilitate or enhance disinfection within a room or area, particularly at distances 1.0, 2.0 or 3.0 meters from apparatus 100, may be included in apparatus 100. Several examples are described above in regard to FIGS. 1-3 and are not reiterated for the sake of brevity. Furthermore, apparatus 100 may include any of the features described in reference to apparatuses described in reference to FIGS. 1-3, including but not limited to energy storage element/s 26, trigger voltage circuitry 28, power circuitry 30, pulse duration circuitry 32, program instructions 34, processor 36, optional battery 38, remote user interface 40, power cord 42, wheels 44, occupancy sensor 46, a user interface on the apparatus (in addition or alternative to remote user interface 40), a handle to aid in portability of the apparatus, a power socket inlet (in addition or alternative to power cord 42) and/or additional sensors, such as additional occupancy sensors and light sensors. Some of such features are not shown in apparatus 100 to simplify the drawing in FIG. 9. Furthermore, some of such features are not described in reference to apparatus 100 for the sake of brevity.

As shown in FIG. 8, apparatus 100 may include power supply circuitry 26, pulse circuitry 108, program instructions 28, processor 30, battery 32, remote user interface 34, and occupancy sensor 48. In general, power supply circuitry 26 is configured to supply power to each of light sources 102 and 112 for operation thereof and pulse circuitry is configured to facilitate pulses of light at germicidal light source 102 and possibly at visible light source 112, depending on whether light from visible light source is to be emitted in recurrent pulses or continuously. In cases in which visible light source 102 is operated to generate visible light continuously, the visible light may serve to substantially mask the visible light generated by the germicidal light source. In contrast, in cases in which visible light source 102 is operated to generate recurrent pulses of visible light, the pulses of visible light from the visible light source may be projected between projections of light from the germicidal light source such that the projections of visible light from the two light sources produces a collective stream of visible light pulsed at a frequency greater than 60 Hz minimizing seizure inducement. In such cases, germicidal light source and the visible light source are pulsed at the same frequency but with a phase difference relative to each other. The pulse durations of the germicidal light source and the visible light source may be the same or different.

Figure 9:
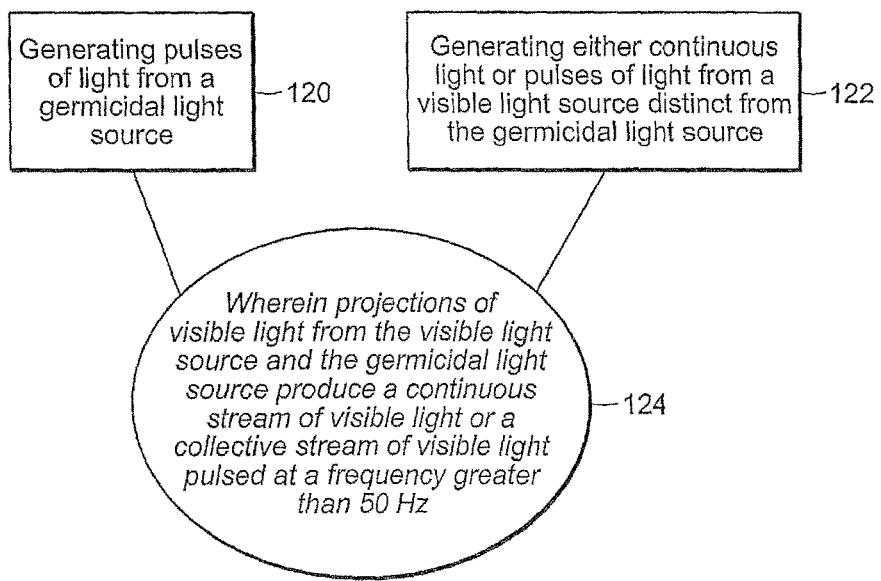
FIG. 9 illustrates a diagram of options for generating light at each of light sources of the apparatus depicted in FIG. 8.

FIG. 9 illustrates a diagram of the two operational options of generating light at each of light sources 102 and 112 with respect to each other. In particular, FIG. 9 shows block 120 denoting that pulse of light are generated at a germicidal light source. In addition, FIG. 9 shows block 122 denoting that light generated at a visible light source distinct from the germicidal light source is generated either continuously or is pulsed. Moreover, FIG. 9 shows block 124 denoting that the generation of light from the two light sources is governed such that projections of visible light from the visible light source and projections of visible light from the germicidal light source produce a continuous stream of visible light or a collective stream of visible light pulsed at a frequency greater than 60 Hz.

As noted above, an optical filter configured to attenuate a majority or all visible light generated from a germicidal light source may be used to mask the generation of visible light from the germicidal light source. It is noted that the use of such an optical filter is not limited to embodiments in which the germicidal light source is pulsed at a frequency between 3 Hz and 50 Hz. In particular, any of the apparatuses described herein may include an optical filter configured to attenuate a majority or all visible light generated from the germicidal light source, regardless of the pulse frequency of light generated therefrom. It is noted, however, that an optical filter configured to attenuate visible light generally reduces the germicidal efficacy of room disinfection apparatuses, particularly at distances at 1, 2 and 3 meters away from a germicidal light source of an apparatus. Thus, in some cases, it may be advantageous to omit an optical filter for attenuating visible light in the apparatuses described herein.

It will be appreciated to those skilled in the art having the benefit of this disclosure that this invention is believed to provide pulsed light disinfection systems and methods which trigger a germicidal pulsed light source at a frequency greater than 3 Hz. Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims. The term "approximately" as used herein refers to variations of up to +/−5% of the stated number.

What is claimed is:

1. A method for reducing bacterial contamination on surfaces in an enclosed space which is suitable for human occupancy, wherein the method comprises:
generating pulses of light at a frequency greater than approximately 20 Hz from a germicidal light source of a disinfection apparatus that is arranged in an enclosed space which is suitable for human occupancy; and
projecting the pulses of light to surfaces in the enclosed space at least 1.0 meter from the disinfection apparatus, wherein the pulses of light generated by the germicidal light source comprise a pulse duration and an energy flux sufficient to generate a power flux between approximately 200 W/m$^2$ and approximately 5000 W/m$^2$ of ultraviolet light in the wavelength range between 200 nm and 320 nm at the surfaces.

2. The method of claim 1, further comprising inhibiting or terminating operation of the disinfection apparatus based on a detection signal from an occupancy sensor comprising the disinfection apparatus.

3. The method of claim 1, wherein the step of projecting the pulses of light comprises projecting the pulses of light directly to surfaces in the enclosed space at least 2.0 meters from the disinfection apparatus.

4. The method of claim 1, wherein the step of generating the pulses of light comprises generating the pulses of light at a frequency greater than approximately 40 Hz.

5. The method of claim 1, wherein the step of generating the pulses of light comprises generating the pulses of light at a frequency greater than approximately 60 Hz.

6. The method of claim 1, wherein the step of generating the pulses of light comprises generating the pulses of light at a frequency between approximately 55 Hz and approximately 80 Hz.

7. The method of claim 1, wherein the step of generating the pulses of light comprises generating the pulses of light at a frequency greater than approximately 80 Hz.

8. The method of claim 1, wherein the pulses of light generated by the germicidal light source comprise a pulse duration and an energy flux sufficient to generate a power flux between approximately 200 W/m$^2$ and approximately 2500 W/m$^2$ of ultraviolet light in the wavelength range between 200 nm and 320 nm at the surfaces.

9. The method of claim 1, wherein the pulses of light generated by the germicidal light source comprise a pulse duration and an energy flux sufficient to generate a power flux between approximately 200 W/m$^2$ and approximately 1000 W/m$^2$ of ultraviolet light in the wavelength range between 200 nm and 320 nm at the surfaces.

10. The method of claim 1, further comprising automatically moving the germicidal light source relative to a support structure of the disinfection apparatus during the steps of generating and projecting the pulses of light.

11. The method of claim 1, further comprising automatically moving the disinfection apparatus during the steps of generating and projecting the pulses of light.

12. The method of claim 1, wherein the germicidal light source is a polychromatic germicidal light source.

13. The method of claim 1, wherein the germicidal light source generates ultraviolet light and visible light, wherein the method further comprises generating pulses of light from a visible light source distinct from the germicidal light source such that combined projections of visible light from the visible light source and the germicidal light source produce a continuous stream of visible light or a collective stream of visible light pulsed at a frequency greater than 50 Hz.

\* \* \* \* \*